United States Patent
Locke et al.

(10) Patent No.: US 11,164,269 B1
(45) Date of Patent: Nov. 2, 2021

(54) SYSTEMS AND METHODS FOR DYNAMIC TRAVEL PLANNING

(71) Applicant: Johnson Controls Tyco IP Holdings LLP, Milwaukee, WI (US)

(72) Inventors: Robert B. Locke, Sonoma, CA (US); Richard J. Campero, Morgan Hill, CA (US); John D. Perkins, Lake Worth, FL (US); Karl F. Reichenberger, Mequon, WI (US)

(73) Assignee: Johnson Controls Tyco IP Holdings LLP, Milwaukee, WI (US)

( * ) Notice: Subject to any disclaimer, the term of this patent is extended or adjusted under 35 U.S.C. 154(b) by 0 days.

(21) Appl. No.: 17/067,230

(22) Filed: Oct. 9, 2020

Related U.S. Application Data

(60) Provisional application No. 63/044,082, filed on Jun. 25, 2020.

(51) Int. Cl.
  *G06Q 10/10* (2012.01)
  *G06Q 30/02* (2012.01)
  (Continued)

(52) U.S. Cl.
  CPC ......... *G06Q 50/14* (2013.01); *G01C 21/3461* (2013.01); *G06F 16/2365* (2019.01);
  (Continued)

(58) Field of Classification Search
  CPC ...... G06Q 50/14; G06Q 50/30; G06Q 50/265; G06Q 10/10; G06Q 10/047; G06Q 10/02;
  (Continued)

(56) References Cited

U.S. PATENT DOCUMENTS

| 6,148,306 A | 11/2000 | Seidl et al. |
| 6,293,861 B1 | 9/2001 | Berry |

(Continued)

FOREIGN PATENT DOCUMENTS

| EP | 1 770 454 A1 | 4/2007 |
| JP | 2010-128976 A | 6/2010 |

(Continued)

OTHER PUBLICATIONS

Angelopoulos, et al., "DHP Framework: Digital Health Passports Using Blockchain—Use case on international tourism during the COVID-19 pandemic," retrieved from https://arxiv.org/abs/2005.08922, 8 pages (2020).

(Continued)

*Primary Examiner* — Jonathan P Ouellette
(74) *Attorney, Agent, or Firm* — Foley & Lardner LLP

(57) ABSTRACT

A system including one or more memory devices having instructions stored thereon, that, when executed by one or more processors, cause the one or more processors to receive travel data associated with a travel plan of a user indicating one or more travel destinations. The instructions cause the one or more processors to receive destination risk data indicating a destination risk of the one or more travel destinations associated with transmission of an infectious disease, receive personal risk data indicating a risk of the user associated with the infectious disease, and generate an infection travel risk score for the user based on the destination risk data and the personal risk data.

28 Claims, 12 Drawing Sheets

(51) Int. Cl.

| | |
|---|---|
| *G06Q 40/08* | (2012.01) |
| *G06Q 10/08* | (2012.01) |
| *G06Q 50/14* | (2012.01) |
| *G16H 50/30* | (2018.01) |
| *G06Q 10/04* | (2012.01) |
| *G16H 10/60* | (2018.01) |
| *G06Q 30/00* | (2012.01) |
| *G06Q 30/06* | (2012.01) |
| *G06Q 50/26* | (2012.01) |
| *G06F 16/23* | (2019.01) |
| *H04L 9/32* | (2006.01) |
| *G01C 21/34* | (2006.01) |
| *G16H 50/80* | (2018.01) |
| *G06Q 10/02* | (2012.01) |

(52) U.S. Cl.
CPC ........... *G06Q 10/047* (2013.01); *G06Q 10/10* (2013.01); *G06Q 30/0185* (2013.01); *G06Q 30/0205* (2013.01); *G06Q 30/0645* (2013.01); *G06Q 50/265* (2013.01); *G16H 10/60* (2018.01); *G16H 50/30* (2018.01); *G16H 50/80* (2018.01); *H04L 9/3247* (2013.01); *G06Q 10/02* (2013.01); *G06Q 2220/00* (2013.01)

(58) Field of Classification Search
CPC ........... G06Q 30/0185; G06Q 30/0205; G06Q 30/0645; G06Q 2220/00; G06F 16/2365; G16H 50/30; G16H 50/80; G16H 10/60; H04L 9/3247
USPC .......................................... 705/1.1–912, 325
See application file for complete search history.

(56) References Cited

U.S. PATENT DOCUMENTS

| | | | |
|---|---|---|---|
| 6,792,319 B1 | 9/2004 | Bilger | |
| 6,909,921 B1 | 6/2005 | Bilger | |
| 7,099,895 B2 | 8/2006 | Dempsey | |
| 7,394,370 B2 | 7/2008 | Chan | |
| 7,817,046 B2 | 10/2010 | Coveley et al. | |
| 7,941,096 B2 | 5/2011 | Perkins et al. | |
| 8,049,614 B2* | 11/2011 | Kahn | G16H 50/80 340/521 |
| 8,405,503 B2 | 3/2013 | Wong | |
| 8,560,339 B2* | 10/2013 | Khan | G16H 50/20 705/2 |
| 8,589,214 B1 | 11/2013 | Scott et al. | |
| 8,867,993 B1 | 10/2014 | Perkins et al. | |
| 8,936,944 B2 | 1/2015 | Peltz et al. | |
| 9,075,909 B2* | 7/2015 | Almogy | G06F 19/00 |
| 9,087,204 B2* | 7/2015 | Gormley | H04L 63/0861 |
| 9,435,659 B1* | 9/2016 | Kozloski | G01C 21/20 |
| 9,459,607 B2 | 10/2016 | Frazer et al. | |
| 9,475,359 B2 | 10/2016 | Mackay | |
| 9,491,574 B2* | 11/2016 | O'Sullivan | H04W 4/02 |
| 9,521,009 B1 | 12/2016 | Skeffington | |
| 9,618,224 B2 | 4/2017 | Emmons et al. | |
| 9,733,656 B2 | 8/2017 | Janoso et al. | |
| 9,945,688 B2* | 4/2018 | Kozloski | G01C 21/3453 |
| 10,068,116 B2 | 9/2018 | Good et al. | |
| 10,156,833 B2 | 12/2018 | Ray et al. | |
| 10,198,779 B2 | 2/2019 | Pittman et al. | |
| 10,234,836 B2 | 3/2019 | Duchene et al. | |
| 10,251,610 B2 | 4/2019 | Parthasarathy et al. | |
| 10,339,484 B2* | 7/2019 | Pai | G06Q 10/0635 |
| 10,389,518 B2* | 8/2019 | Chen | H04L 9/3236 |
| 10,885,170 B1* | 1/2021 | Maliani | G06Q 50/00 |
| 2002/0084900 A1 | 7/2002 | Peterson et al. | |
| 2004/0163325 A1 | 8/2004 | Parrini et al. | |
| 2004/0172277 A1 | 9/2004 | Dione | |
| 2004/0267385 A1 | 12/2004 | Lingemann | |
| 2006/0218010 A1* | 9/2006 | Michon | G16H 50/30 705/3 |
| 2007/0219645 A1 | 9/2007 | Thomas et al. | |
| 2007/0222599 A1 | 9/2007 | Coveley et al. | |
| 2007/0226291 A1 | 9/2007 | Lundblad et al. | |
| 2008/0277486 A1 | 11/2008 | Seem et al. | |
| 2008/0281472 A1 | 11/2008 | Podgorny et al. | |
| 2009/0070134 A1 | 3/2009 | Rodgers | |
| 2009/0105995 A1 | 4/2009 | Harrington | |
| 2009/0210262 A1* | 8/2009 | Rines | G06Q 10/06 705/5 |
| 2009/0299767 A1* | 12/2009 | Michon | G16H 50/80 705/3 |
| 2009/0300174 A1 | 12/2009 | Floris et al. | |
| 2010/0179832 A1 | 7/2010 | Van Deursen et al. | |
| 2010/0262298 A1 | 10/2010 | Johnson et al. | |
| 2010/0280636 A1 | 11/2010 | Holland et al. | |
| 2010/0307731 A1 | 12/2010 | Yonezawa et al. | |
| 2010/0324962 A1 | 12/2010 | Nesler et al. | |
| 2011/0047418 A1 | 2/2011 | Drees et al. | |
| 2011/0087650 A1 | 4/2011 | Mackay et al. | |
| 2011/0093126 A1 | 4/2011 | Toba et al. | |
| 2011/0178977 A1 | 7/2011 | Drees | |
| 2011/0313808 A1 | 12/2011 | Kavanagh et al. | |
| 2012/0001487 A1 | 1/2012 | Pessina | |
| 2012/0029661 A1 | 2/2012 | Jones et al. | |
| 2012/0029970 A1* | 2/2012 | Stiles | G06Q 10/06 705/7.28 |
| 2012/0079407 A1 | 3/2012 | Holmes et al. | |
| 2012/0083937 A1 | 4/2012 | Kong et al. | |
| 2012/0197896 A1* | 8/2012 | Li | G06F 16/313 707/740 |
| 2013/0036139 A1* | 2/2013 | Kung | G06Q 10/025 707/780 |
| 2013/0079471 A1 | 3/2013 | Brown et al. | |
| 2013/0166607 A1* | 6/2013 | Turk | G06Q 10/02 707/803 |
| 2013/0218349 A1 | 8/2013 | Coogan et al. | |
| 2013/0257626 A1 | 10/2013 | Masli et al. | |
| 2013/0268128 A1 | 10/2013 | Casilli et al. | |
| 2013/0297259 A1 | 11/2013 | Tsao et al. | |
| 2014/0023363 A1 | 1/2014 | Apte | |
| 2014/0167917 A2* | 6/2014 | Wallace | G16H 40/67 340/10.1 |
| 2014/0188541 A1* | 7/2014 | Goldsmith | H04L 67/306 705/7.19 |
| 2014/0195664 A1 | 7/2014 | Rahnama | |
| 2014/0277765 A1 | 9/2014 | Karimi et al. | |
| 2014/0316582 A1 | 10/2014 | Berg-Sonne et al. | |
| 2014/0350970 A1* | 11/2014 | Schumann, Jr. | G06Q 40/08 705/4 |
| 2014/0368601 A1* | 12/2014 | deCharms | H04W 4/029 348/14.02 |
| 2015/0005900 A1 | 1/2015 | Steele et al. | |
| 2015/0032265 A1 | 1/2015 | Herring et al. | |
| 2015/0066169 A1 | 3/2015 | Nakano et al. | |
| 2015/0088570 A1 | 3/2015 | Yenni et al. | |
| 2015/0100330 A1* | 4/2015 | Shpits | G16H 50/80 705/2 |
| 2015/0140990 A1 | 5/2015 | Kim et al. | |
| 2015/0159893 A1 | 6/2015 | Daubman et al. | |
| 2015/0168926 A1 | 6/2015 | Wood | |
| 2015/0285527 A1 | 10/2015 | Kim et al. | |
| 2015/0293508 A1 | 10/2015 | Piaskowski et al. | |
| 2015/0312696 A1 | 10/2015 | Ribbich et al. | |
| 2015/0319176 A1 | 11/2015 | Yahalom et al. | |
| 2015/0370927 A1 | 12/2015 | Flaherty et al. | |
| 2016/0005300 A1 | 1/2016 | Laufer et al. | |
| 2016/0020918 A1 | 1/2016 | Lu | |
| 2016/0095188 A1 | 3/2016 | Verberkt et al. | |
| 2016/0117616 A1* | 4/2016 | Wang | G06Q 10/025 705/6 |
| 2016/0127174 A1 | 5/2016 | Fu et al. | |
| 2016/0147207 A1 | 5/2016 | Park et al. | |
| 2016/0258641 A1 | 9/2016 | Cheatham et al. | |
| 2016/0282825 A1 | 9/2016 | Kariguddaiah | |
| 2016/0306934 A1 | 10/2016 | Sperry et al. | |
| 2016/0320760 A1 | 11/2016 | Brun et al. | |

(56) References Cited

U.S. PATENT DOCUMENTS

| | | |
|---|---|---|
| 2017/0026194 A1 | 1/2017 | Vijayrao et al. |
| 2017/0041296 A1* | 2/2017 | Ford ................... H04L 63/0421 |
| 2017/0076042 A1 | 3/2017 | Katz et al. |
| 2017/0103633 A1 | 4/2017 | Khire et al. |
| 2017/0124842 A1 | 5/2017 | Sinha et al. |
| 2017/0178037 A1* | 6/2017 | Kaye ................... G06Q 10/047 |
| 2017/0191695 A1 | 7/2017 | Bruhn et al. |
| 2017/0195130 A1 | 7/2017 | Landow et al. |
| 2017/0206334 A1 | 7/2017 | Huang |
| 2017/0234067 A1 | 8/2017 | Fasi et al. |
| 2017/0281819 A1 | 10/2017 | Jones et al. |
| 2017/0350615 A1 | 12/2017 | Ashar |
| 2017/0351831 A1* | 12/2017 | Cahan ................... G06Q 50/14 |
| 2017/0351832 A1* | 12/2017 | Cahan ................... G16H 70/60 |
| 2017/0351833 A1* | 12/2017 | Cahan ................... G16H 50/30 |
| 2017/0351834 A1* | 12/2017 | Cahan ................... G16H 50/50 |
| 2017/0352119 A1 | 12/2017 | Pittman et al. |
| 2017/0366414 A1 | 12/2017 | Hamilton et al. |
| 2018/0005195 A1 | 1/2018 | Jacobson |
| 2018/0046766 A1* | 2/2018 | Deonarine ............. G06F 21/62 |
| 2018/0052970 A1* | 2/2018 | Boss ................... G16H 50/30 |
| 2018/0101146 A1 | 4/2018 | Hariharan et al. |
| 2018/0113897 A1 | 4/2018 | Donlan et al. |
| 2018/0120778 A1 | 5/2018 | Billings |
| 2018/0120788 A1 | 5/2018 | Billings |
| 2018/0191197 A1 | 7/2018 | Carr et al. |
| 2018/0210438 A1 | 7/2018 | Ashar et al. |
| 2018/0225606 A1 | 8/2018 | Curcic et al. |
| 2018/0247476 A1 | 8/2018 | Kusens et al. |
| 2018/0270063 A1 | 9/2018 | Bard et al. |
| 2018/0276775 A1 | 9/2018 | Khurana et al. |
| 2018/0299845 A1 | 10/2018 | Ray et al. |
| 2018/0314277 A1 | 11/2018 | Moore et al. |
| 2018/0375444 A1 | 12/2018 | Gamroth |
| 2019/0011894 A1 | 1/2019 | Meyer et al. |
| 2019/0033802 A1 | 1/2019 | Chatterjee et al. |
| 2019/0095874 A1 | 3/2019 | Bellrose et al. |
| 2019/0122759 A1 | 4/2019 | Wakimoto |
| 2019/0155268 A1 | 5/2019 | Cohen et al. |
| 2019/0158431 A1 | 5/2019 | Meyer et al. |
| 2019/0188616 A1* | 6/2019 | Urban ................ G06Q 10/0875 |
| 2019/0188977 A1 | 6/2019 | Moses et al. |
| 2019/0203532 A1 | 7/2019 | Feldstein |
| 2019/0250575 A1 | 8/2019 | Jonsson |
| 2020/0009280 A1 | 1/2020 | Kupa |
| 2020/0176124 A1 | 6/2020 | Chatterjea et al. |
| 2020/0176125 A1 | 6/2020 | Chatterjea et al. |
| 2020/0194103 A1* | 6/2020 | Weldemariam ......... H04W 4/14 |
| 2020/0219623 A1 | 7/2020 | Kushida |
| 2020/0225313 A1 | 7/2020 | Coles |
| 2020/0226892 A1 | 7/2020 | Coles |
| 2020/0227160 A1 | 7/2020 | Youngblood et al. |
| 2020/0264572 A1 | 8/2020 | Sha et al. |
| 2020/0294680 A1 | 9/2020 | Gupta et al. |
| 2020/0327434 A1 | 10/2020 | Maeser |
| 2020/0365260 A1 | 11/2020 | Sperry et al. |
| 2021/0018884 A1 | 1/2021 | Kupa et al. |
| 2021/0020285 A1 | 1/2021 | Hall |

FOREIGN PATENT DOCUMENTS

| | | |
|---|---|---|
| KR | 20200047457 A | 5/2020 |
| WO | WO-2010/141601 A2 | 12/2010 |
| WO | WO-2016/180754 A1 | 11/2016 |
| WO | WO-2017/007418 | 1/2017 |

OTHER PUBLICATIONS

Brownstein, et al., "Empirical Evidence for the Effect of Airline Travel on Inter-Regional Influenza Spread in the United States," PLoS Medicine, 3(10), e401, pp. 1826-1835 (Oct. 2006).

Conley, "Encryption, Hashing, PPK, and Blockchain: A Simple Introduction," Vanderbilt University Department of Economics Working Papers, VUECON-19-00013, 14 pages (Aug. 17, 2019).

Jacobson, et al., "A double-risk monitoring and movement restriction policy for Ebola entry screening at airports in the United States," Preventative Medicine, 88, pp. 33-38 (2016).

Miraz et al., "Applications of Blockchain Technology beyond Cryptocurrency," Annals of Emerging Technologies in Computing, 2(1), pp. 1-6 (2018).

Sandhu, et al., "An intelligent system for predicting and preventing MERS-CoV infection outbreak," The Journal of Supercomputing, 72, pp. 3033-3056 (2016).

Wikipedia, "Manifest (transportation)," retrieved from https://en.wikipedia.org/wiki/Manifest_(transportation), 3 pages (2020).

U.S. Appl. No. 16/927,759, filed Jul. 13, 2020, Johnson Controls Technology Co.

U.S. Appl. No. 16/927,766, filed Jul. 13, 2020, Johnson Controls Technology Co.

U.S. Appl. No. 16/984,945, filed Aug. 4, 2020, Johnson Controls Tech Co.

"Ambient (outdoor) air pollution," WHO, URL: https://www.who.int/en/news-room/fact-sheets/detail/ambient-(outdoor)-air-quality-and-health, May 2, 2018, 9 pages.

"ASHRAE Epidemic Task Force Established," ASHRAE, URL: https://www.ashrae.org/about/news/2020/ashrae-epidemic-task-force-established, Mar. 31, 2020, 6 pages.

"ASHRAE Issues Statements on Relationship Between COVID-19 and HVAC in Buildings," ASHRAE, URL: https://www.ashrae.org/about/news/2020/ashrae-issues-statements-on-relationship-between-covid-19-and-hvac-in-buildings, Apr. 20, 2020, 6 pages.

"ASHRAE Offers COVID-19 Building Readiness/Reopening Guidance," ASHRAE, URL: https://www.ashrae.org/about/news/2020/ashrae-offers-covid-19-building-readiness-reopening-guidance, May 7, 2020, 6 pages.

"ASHRAE Resources Available to Address COVID-19 Concerns," ASHRAE, URL: https://www.ashrae.org/about/news/2020/ashrae-resources-available-to-address-covid-19-concerns, Feb. 27, 2020, 6 pages.

Building Readiness, ASHRAE Epidemic Task Force, URL: https://www.ashrae.org/file%20library/technical%20resources/covid-19/ashrae-building-readiness.pdf, Aug. 19, 2020, 119 pages.

"Carbon Monoxide Levels & Risks," The National Comfort Institute, URL: https://www.myhomecomfort.org/carbon-monoxide-levels-risks/, Retrieved on Sep. 3, 2020, 4 pages.

"Coronavirus (COVID-19) Response Resources from ASHRAE and Others," ASHRAE, URL: https://www.ashrae.org/technical-resources/resources, Retrieved Sep. 3, 2020, 27 pages.

"Environmental Health Committee (EHC) Emerging Issue Brief: Pandemic COVID-19 and Airborne Transmission," ASHRAE, URL: https://www.ashrae.org/file%20library/technical%20resources/covid-19/eiband-airbornetransmission.pdf, Apr. 17, 2020, 3 pages.

"Filtration & Disinfection," ASHRAE Epidemic Task Force, URL: https://www.ashrae.org/file%20library/technical%20resources/covid-19/ashrae-filtration_disinfection-c19-guidance.pdf, Aug. 7, 2020, 37 pages.

"Guidance for Polling Place HVAC Systems," ASHRAE, URL: https://www.ashrae.org/file%20library/technical%20resources/covid-19/guidance-for-polling-place-hvac-systems.pdf, Retrieved Sep. 3, 2020, 2 pages.

"Guidance for the Re-Opening of Schools," ASHRAE, URL: https://www.ashrae.org/file%20library/technical%20resources/covid-19/guidance-for-the-re-opening-of-schools.pdf, Retrieved Sep. 3, 2020, 1 page.

"Making Polling Places Safer," ASHRAE, URL: https://www.ashrae.org/about/news/2020/making-polling-places-safer, Aug. 20, 2020, 6 pages.

"Researchers are working to develop smart ventilation control system for buildings," News Medical, URL: https://www.news-medical.net/news/20200520/Researchers-are-working-to-develop-smart-ventilation-control-system-for-buildings.aspx?MvBriefArticleId=1693, May 20, 2020, 2 pages.

"Schools & Universities," ASHRAE Epidemic Task Force, URL: https://www.ashrae.org/file%20library/technical%20resources/covid-19/ashrae-reopening-schools.pdf, May 5, 2020, 33 pages.

(56) References Cited

OTHER PUBLICATIONS

"Science has shown us three reasons why we should always maintain 40-60%RH in public buildings like hospitals, schools and offices, throughout the year," URL: https://40to60rh.com/, Retrieved Sep. 3, 2020, 9 pages.
Anonymous: "Delta Building Management and Controls System". Internet Article. Retrieved from the Internet: URL:http://www.deltaww.com/filecenter/solu tions/download/05/Delta BMCS LDALISolution Guide 201608 eng.pdf?CID=23, Sep. 1, 2016, 17 pages.
Goldstein, "Increased indoor humidity may decrease #Coronavirus #COVID-19 transmission," WUWT: Watts Up With That?, URL: 2https://wattsupwiththat.com/2020/03/28/increased-indoor-humidity-may-decrease-coronavirus-covid-19-transmission/, Mar. 28, 2020, 91 pages.
International Search Report and Written Opinion on PCT/US2018/027396, dated Jun. 27, 2018. 16 pages.
International Search Report and Written Opinion on PCT/US2018/051182, dated Nov. 22, 2018, 17 pages.
Levin, "Preprocessing Data", URL: https://www.percona.com/blog/2011/08/08/preprocessingdata/, Aug. 8, 2011, 5 pages.
Office Action on EP 18721926.6, dated Aug. 12, 2020, 8 pages.
Riley et al., "Airborne Spread of Measles in a Suburban Elementary School," American Journal of Epidemiology, 1978, 107:5, pp. 421-432.
Rowland, "Designing Connected products: UX for the Consumer Internet of Things," May 31, 2015, pp. 2, 5-6, 8-14, 32-35,48-9, 52, 93, 95-99, 123, 307, 312, 395, 532, 613-625.
Sinopoli, "Smart Buildings Systems for Architects, Owners and Builders," Nov. 18, 2009, chapters 3, 4, 5 and 6, pp. 3-8, 129-136.
Sterling et al., "Criteria for Human Exposure to Humidity on Occupied Buildings," ASHRAE Transactions, 1985, vol. 91, Part 1, CH85-13 No. 1, pp. 611-622.
Wikipedia: "Building automation," URL:https://en.wikipedia.org/w/index.php?title=Buildingautomation&oldid=799424260, Sep. 7, 2017. 12 pages.
Wikipedia: "Building management system," URL:https://en.wikipedia.org/w/index.php?title=Building managementsystem&oldid=797980461, Aug. 30, 2017, 4 pages.
Yeh et al., "iPower: An Energy Conservation System for Intelligent Buildings by Wireless Sensor Networks," Inderscience Intl Jrnl of Sensor Networks, Year 2009, 9 pages.
Rifi et al., "Towards Using Blockchain Technology for eHealth Data Access Management," 2017 Fourth International Conference on Advances in Biomedical Engineering (ICABME), 2017, 4 pages.

* cited by examiner

US 11,164,269 B1

SYSTEMS AND METHODS FOR DYNAMIC TRAVEL PLANNING

CROSS-REFERENCE TO RELATED PATENT APPLICATION

This application claims the benefit of and priority to U.S. Provisional Application No. 63/044,082 filed Jun. 25, 2020, the entirety of which is incorporated by reference herein.

BACKGROUND

The present disclosure relates generally to risk analysis systems for disease related risks. Some diseases, e.g., viruses, bacterial infections, etc. can significantly affect the health of people, or certain classes of people, who contract the disease. It may be beneficial to take measures that restrict the ability of a healthy person from contracting the disease or an infected person from spreading the disease. For example, behaviors such as wearing masks, practicing social distancing techniques, using alcohol based hand sanitizers, washing hands, self-quarantining when sick, avoiding high infection areas, and other behaviors can reduce the spread of the disease.

SUMMARY

Dynamic Travel Planning Based on Risk

One implementation of the present disclosure is a system including one or more memory devices having instructions stored thereon, that, when executed by one or more processors, cause the one or more processors to receive travel data associated with a travel plan of a user indicating one or more travel destinations. The instructions cause the one or more processors to receive destination risk data indicating a destination risk of the one or more travel destinations associated with transmission of an infectious disease, receive personal risk data indicating a risk of the user associated with the infectious disease, and generate an infection travel risk score for the user based on the destination risk data and the personal risk data.

In some embodiments, the instructions cause the one or more processors to generate one or more suggestions to the travel plan based on the infection travel risk score increasing to a value greater than a particular amount caused by at least one of a first change to the destination risk data or a second change to the personal risk data.

In some embodiments, the instructions cause the one or more processors to generate travel routes from an originating location to the one or more travel destinations, generate infection route risk scores for the travel routes and perform at least one of generating a suggestion for the user to travel on one of the travel routes associated with a lowest infection route risk score, generating a user interfacing including an indication of the travel routes and the infection route risk scores, or generating a list including the travel routes ranked according to the infection route risk scores associated with the travel routes.

In some embodiments, the personal risk data indicates whether the user has previously contracted and recovered from the infectious disease.

In some embodiments, the instructions cause the one or more processors to receive a request for the infection travel risk score from an external system, wherein the external system sends the request to the one or more processors in response to a user device of the user requesting access from the external system to a service or location and communicate the infection travel risk score to the external system in response to receiving the request from the external system.

In some embodiments, the instructions cause the one or more processors to receive a request to share the infection travel risk score from a user device of the user with a second user device or an external system and responsive to receiving the request, perform at least one of sending the infection travel risk score to the user device, second user device, or the second external system or generating a shareable link to a data source storing the infection travel risk score and send the link to the user device.

In some embodiments, the instructions cause the one or more processors to receive a manifest from a user device of the user representing a travel activity performed by the user, receive a second manifest from a blockchain, wherein the second manifest is a copy of the manifest, wherein the second manifest is stored in the blockchain by an external system to create a record of the travel activity performed by the user, validate the manifest received from the user device with the second manifest of the blockchain, and generate the infection travel risk score for the user based on the travel activity represented by the manifest.

In some embodiments, the second manifest includes a first signature of the user device and a second signature of the external system. In some embodiments, the instructions cause the one or more processors to determine that the first signature is authentic with a first public key of the user device and determine that the second signature is authentic with a second public key of the external system.

In some embodiments, the second manifest is hashed by the external system. In some embodiments, the instructions cause the one or more processors to validate the manifest received from the user device by determining that the manifest matches the second manifest by hashing the manifest received from the user device and comparing a hash of the manifest received from the user device to the second manifest hashed by the external system.

In some embodiments, the instructions cause the one or more processors to generate a travel itinerary for the user based on the travel data and risk data associated with the travel plan and provide the travel itinerary to the user via a user interface of a user device, generate one or more suggested updates to the travel itinerary based on changes in the risk data to dynamically account for changes in the risk data as the user is traveling, and provide the one or more suggested updates to the user via the user interface of the user device.

In some embodiments, the instructions cause the one or more processors to generate the travel itinerary based on disparate factors including travel modes, travel destinations, and stops along a travel route.

In some embodiments, the risk data indicates disease infection risk indicating a likelihood of the user contracting the infectious disease.

In some embodiments, the risk data is received by the one or more processors as risk events from at least one of an event notification system, a contact tracing system, or a health authority system.

In some embodiments, the risk data is contact tracing data, wherein the contact tracing data indicates at least one of one or more past locations or one or more future locations of a person infected by the infectious disease. In some embodiments, the instructions cause the one or more processors to perform at least one of generating the travel itinerary to include one or more transportation selections that avoid at least one of the one or more past locations or the one or more future locations of the person infected by the infectious disease or updating a value of the infection travel risk score based on the contact tracing data.

In some embodiments, the instructions cause the one or more processors to determine risk values associated with dining options, select one or more dining options from the dining options based on the risk values associated with the dining options, and cause the travel itinerary to include the one or more dining options.

In some embodiments, the instructions cause the one or more processors to determine risk values associated with overnight stay accommodation options, select one or more overnight stay accommodations from the overnight stay accommodation options based on the risk values associated with the overnight stay accommodation options, and cause the travel itinerary to include the one or more overnight stay accommodations.

In some embodiments, the risk data indicates a threat level associated with geographic areas. In some embodiments, the instructions cause the one or more processors to generate the travel itinerary by determining one or more travel routes through one or more low risk geographic areas associated with threat levels less than one or more other high risk geographic areas. In some embodiments, the threat levels associated with the geographic areas indicate a disease infection level of people within the geographic areas.

In some embodiments, the travel itinerary includes one or more transportation selections. In some embodiments, the instructions cause the one or more processors to select the one or more transportation selections from transportation options based on transportation risk data associated with the transportation options.

In some embodiments, the one or more transportation selections include one or more car rental selections. In some embodiments, the instructions cause the one or more processors to select the one or more car rental selections from car rental options based on a health safety ratings of the car rental options.

In some embodiments, the one or more transportation selections include one or more flight transportation selections. In some embodiments, the transportation risk data associated with the transportation options includes one or more of a length of a flight layover, a distance between two flight gates of a connecting flight, a likelihood of the user needing to eat during the traveling of the user, or an indication of infected individuals booked for a particular flight.

Another implementation of the present disclosure is a method including receiving, by a processing circuit, travel data associated with a travel plan of a user indicating one or more travel destinations and receiving, by the processing circuit, destination risk data indicating a destination risk of the one or more travel destinations associated with transmission of an infectious disease. The method includes receiving, by the processing circuit, personal risk data indicating a risk of the user associated with the infectious disease and generating, by the processing circuit, an infection travel risk score for the user based on the destination risk data and the personal risk data.

In some embodiments, the method includes generating, by the processing circuit, one or more suggestions to the travel plan based on the infection travel risk score increasing to a value greater than a particular amount caused by at least one of a first change to the destination risk data or a second change to the personal risk data.

In some embodiments, the method includes generating, by the processing circuit, travel routes from an originating location to the one or more travel destinations, generating, by the processing circuit, infection route risk scores for the travel routes, and performing, by the processing circuit, at least one of generating a suggestion for the user to travel on one of the travel routes associated with a lowest infection route risk score, generating a user interfacing including an indication of the travel routes and the infection route risk scores, or generating a list including the travel routes ranked according to the infection route risk scores associated with the travel routes.

In some embodiments, the method includes generating, by the processing circuit, a travel itinerary for the user based on the travel data and risk data associated with the travel plan and provide the travel itinerary to the user via a user interface of a user device, generating, by the processing circuit, one or more suggested updates to the travel itinerary based on changes in the risk data to dynamically account for changes in the risk data as the user is traveling, and providing, by the processing circuit, the one or more suggested updates to the user via the user interface of the user device.

In some embodiments, the risk data indicates disease infection risk indicating a likelihood of the user contracting the infectious disease.

In some embodiments, the risk data is received by the processing circuit as risk events from at least one of an event notification system, a contact tracing system, or a health authority system.

Another implementation of the present disclosure is a system including one or more memory devices having instructions stored thereon and one or more processors configured to execute the instructions. The instructions cause the one or more processors to receive travel data associated with a travel plan of a user indicating one or more travel destinations, receive destination risk data indicating a destination risk of the one or more travel destinations associated with transmission of an infectious disease, receive personal risk data indicating a risk of the user associated with the infectious disease, and generate an infection travel risk score for the user based on the destination risk data and the personal risk data.

In some embodiments, the instructions cause the one or more processors to generate one or more suggestions to the travel plan based on the infection travel risk score increasing to a value greater than a particular amount caused by at least one of a first change to the destination risk data or a second change to the personal risk data.

In some embodiments, the instructions cause the one or more processors to generate travel routes from a originating location to the one or more travel destinations, generate infection route risk scores for the travel routes, and perform at least one of generating a suggestion for the user to travel on one of the travel routes associated with a lowest infection route risk score, generating a user interface including an indication of the travel routes and the infection route risk scores, or generating a list including the travel routes ranked according to the infection route risk scores associated with the travel routes.

In some embodiments, the instructions cause the one or more processors to receive a manifest from a user device of the user representing a travel activity performed by the user, receive a second manifest from a blockchain, wherein the second manifest is a copy of the manifest, wherein the second manifest is stored in the blockchain by an external system to create a record of the travel activity performed by the user, validate the manifest received from the user device with the second manifest of the blockchain, and generate the infection travel risk score for the user based on the travel activity represented by the manifest.

Trusted Provider Network

One implementation of the present disclosure is a system including one or more memory devices having instructions thereon, that, when executed by one or more processors, cause the one or more processors to receive a request from a service provider to be added to a trusted network of service providers and receive health safety data of a health data stream associated with the service provider and risk data of a risk data stream indicating risk levels associated with the service provider. The instructions cause the one or more processors to determine that the service provider meets a level of heath safety by correlating the health safety data of the health data stream with the risk data of the risk data stream, receive a request from a device for a service provider recommendation of the trusted network of service providers, and provide an indication of the service provider to the device in response to a reception of the request for the service provider recommendation.

In some embodiments, the health data stream indicates factors that reduce a likelihood of a spread of a disease to users at a physical location of the service provider. In some embodiments, the risk data stream indicates risk factors that increase the likelihood of the spread of the disease at the physical location of the service provider.

In some embodiments, the device is a user device of a user, wherein the user requests the service provider to procure a product or service of the service provider.

In some embodiments, the device is a service provider device of a second service provider of the trusted network of service providers, wherein the second service provider requests the service provider to partner with the service provider.

In some embodiments, the instructions cause the one or more processors to add the service provider to a list of the trusted network of service providers in response to a determination that the service provider meets the level of heath safety, receive second health safety data associated with a second service provider of the trusted network of service providers, determine, based on an analysis of the second heath safety data, that the second service provider has a particular health safety level less than the level of heath safety, and remove the second service provider from the list of the trusted network of service providers.

In some embodiments, the health safety data associated with the service provider indicates a health level of each of employees associated with the service provider.

In some embodiments, the health safety data associated with the service provider indicates one or more cleaning procedures performed at a physical location of the service provider.

In some embodiments, the health safety data associated with the service provider is received from a health inspector user device of a health inspector, wherein the health safety data indicates a result of a health inspection performed by the health inspector.

In some embodiments, the health safety data includes surveillance video data of a physical location associated with the service provider, wherein the surveillance video data indicates whether one or more health procedures are followed at the physical location.

In some embodiments, the health safety data indicates whether one or more restricted shopping times are offered at a physical location of the service provider for customers associated with a level of personal health safety above a predefined amount.

In some embodiments, the trusted network of service providers include at least one of an airline, a hotel, a car rental service, a brick and mortar retail store, or a commercial business.

In some embodiments, the risk data indicates disease infection levels in a geographic area associated with the service provider.

In some embodiments, the risk data indicates a number of infected individuals within a physical location of the service provider.

In some embodiments, the health safety data indicates whether the employees have previously contracted and recovered from an infectious disease.

In some embodiments, the instructions cause the one or more processors to receive a manifest from the service provider, the manifest indicating at least one of the health safety data or the risk data, receive a second manifest from a blockchain, wherein the second manifest is a copy of the manifest, wherein the second manifest is stored in the blockchain by an external system to create a record of the health safety data or the risk data, validate the manifest received from the service provider with the second manifest of the blockchain, and determine that the service provider meets a level of heath safety by correlating the health safety data with the risk data in response to validating the manifest.

In some embodiments, the second manifest includes a first signature of the service provider and a second signature of the external system. In some embodiments, the instructions cause the one or more processors to determine that the first signature is authentic with a first public key of the service provider and determine that the second signature is authentic with a second public key of the external system.

In some embodiments, the second manifest is hashed by the external system. In some embodiments, the instructions cause the one or more processors to validate the manifest received from the service provider by determining that the manifest matches the second manifest by hashing the manifest received from the service provider and comparing a hash of the manifest received from the service provider to the second manifest hashed by the external system.

Another implementation of the present disclosure is a system including one or more memory devices having instructions thereon, that, when executed by one or more processors, cause the one or more processors to store a trusted network of service providers in the one or more memory devices, the trusted network of service providers including service providers and receive a request by a first service provider of the service providers for risk data of a second service provider of the service providers. The instructions cause the one or more processors to determine that the first service provider is assigned access to the risk data of the second service provider and provide the first service provider the risk data of the second service provider in response to a determination that the first service provider is assigned access to the risk data of the second service provider.

In some embodiments, the instructions cause the one or more processors to receive a request by the second service provider for first risk data of the first service provider, determine that the second service provider is assigned access to the first risk data of the first service provider, and provide the second service provider the first risk data of the first service provider in response to a particular determination that the second service provider is assigned access to the first risk data of the first service provider.

In some embodiments, the risk data indicates a risk level associated with an asset of the second service provider.

In some embodiments, the risk level indicates risk associated with a physical room associated with the second service provider, a physical location associated with the second service provider, or a vehicle associated with the second service provider.

In some embodiments, the risk data includes health data that indicates factors that reduce a likelihood of a spread of a disease to users at a physical location of the second service provider. In some embodiments, the risk data includes risk related data that indicates risk factors that increase the likelihood of the spread of the disease at the physical location of the second service provider.

In some embodiments, the trusted network of service providers indicates that the first service provider is granted access to a first set of service providers of the service providers and is denied access to a second set of service providers of the service providers.

Another implementation of the present disclosure is a method including receiving, by a processing circuit, a request from a service provider to be added to a trusted network of service providers and receiving, by the processing circuit, health safety data of a health data stream associated with the service provider and risk data of a risk data stream indicating risk levels associated with the service provider. The method includes determining, by the processing circuit, that the service provider meets a level of heath safety by correlating the health safety data of the health data stream with the risk data of the risk data stream, receiving, by the processing circuit, a request by the service provider for risk data of a second service provider of the trusted network of service providers, determining, by the processing circuit, that the service provider is assigned access to the risk data of the second service provider, and providing, by the processing circuit, the service provider the risk data of the second service provider in response to a determination that the service provider is assigned access to the risk data of the second service provider.

In some embodiments, the health data stream indicates factors that reduce a likelihood of a spread of a disease to users at a physical location of the service provider. In some embodiments, the risk data stream indicates risk factors that increase the likelihood of the spread of the disease at the physical location of the service provider.

In some embodiments, the method includes adding, by the processing circuit, the service provider to a list of the trusted network of service providers in response to a second determination that the service provider meets the level of heath safety, receiving, by the processing circuit, second health safety data associated with the second service provider of the trusted network of service providers, determining, by the processing circuit, based on an analysis of the second heath safety data, that the second service provider has a particular health safety level less than the level of heath safety, and removing, by the processing circuit, the second service provider from the list of the trusted network of service providers.

In some embodiments, the method includes receiving, by the processing circuit, a manifest from the service provider, the manifest indicating at least one of the health safety data or the risk data, receiving, by the processing circuit, a second manifest from a blockchain, wherein the second manifest is a copy of the manifest, wherein the second manifest is stored in the blockchain by an external system to create a record of the health safety data or the risk data, validating, by the processing circuit, the manifest received from the service provider with the second manifest of the blockchain, and determining, by the processing circuit, that the service provider meets a level of heath safety by correlating the health safety data with the risk data in response to validating the manifest.

Trusted Consumer Service

One implementation of the present disclosure is a system including one or more memory devices having instructions stored thereon, that, when executed by one or more processors, cause the one or more processors to receive a request from a user device of a user to add the user to a trusted user service associated with a provider of goods or services and receive health behavior data of a health behavior data stream associated with behavior relating to a spread of an infectious disease at a physical location. The instructions cause the one or more processors to determine whether the user meets one or more health safety levels based on the health behavior data stream, add the user to the trusted user service in response to a determination that the user meets the one or more health safety levels, and generate an access indication of access to the physical location at one or more particular times in response to the determination that the user meets the one or more health safety levels.

In some embodiments, the instructions cause the one or more processors to provide the access indication to a user device of the user, wherein the access indication is at least one of a credential, an access password, or an identifier.

In some embodiments, the instructions cause the one or more processors to add the user to a trusted shopper list of trusted shoppers in response to the determination that the user meets one or more health safety rules, receive second health behavior data associated with a second user of the trusted shopper list of trusted shoppers, determine, based on an analysis of the second heath behavior data, that the second user has broken one or more health safety rules, and remove the second user from the trusted shopper list of trusted shoppers in response to a second determination that the second user has broken one or more health safety rules.

In some embodiments, the instructions cause the one or more processors to receive a service provider request for a particular service provider of a list of trusted service providers from the user device, verify that the user of the user device has access to the list of trusted service provider, and provide an indication of the particular service provider to the user device.

In some embodiments, the instructions cause the one or more processors to receive risk data of a risk data stream indicating risk levels associated with the user. In some embodiments, the instructions cause the one or more processors to determine whether the user meets one or more health safety levels by correlating the health behavior data of the health behavior data stream with the risk data of the risk data stream.

In some embodiments, the risk data indicates at least one of disease infection levels of one or more geographic areas that the user has been present within during a particular period of time or contact of the user with one or more infected persons.

In some embodiments, the access indication is associated with access to the physical location at one or more restricted hours restricted for members of the trusted user service.

In some embodiments, the instructions cause the one or more processors to provide an identity of the user to a physical location system of the physical location, wherein the physical location system is configured to receive the identity of the user via one or more sensing devices of the physical location and operate one or more doors to provide the user access to the physical location based on the identity of the user.

In some embodiments, the health behavior data is received from a surveillance system and is video data of the user at the physical location. In some embodiments, the instructions cause the one or more processors to determine whether the health behavior data meets one or more health safety levels by analyzing the video data to determine whether the user follows one or more health safety rules within the physical location.

In some embodiments, the one or more health safety rules include one or more social distancing guidelines, use of a mask, or use of sanitization within the physical location.

In some embodiments, the instructions cause the one or more processors to receive a manifest from a user device of the user representing a travel activity performed by the user, receive a second manifest from a blockchain, wherein the second manifest is a copy of the manifest, wherein the second manifest is stored in the blockchain by an external system to create a record of the travel activity performed by the user, validate the manifest received from the user device with the second manifest of the blockchain, and determine whether the user meets one or more health safety levels based on the health behavior data stream and the travel activity.

In some embodiments, the second manifest includes a first signature of the user device and a second signature of the external system. In some embodiments, the instructions cause the one or more processors to determine that the first signature is authentic with a first public key of the user device and determine that the second signature is authentic with a second public key of the external system.

In some embodiments, the second manifest is hashed by the external system. In some embodiments, the instructions cause the one or more processors to validate the manifest received from the user device by determining that the manifest matches the second manifest by hashing the manifest received from the user device and comparing a hash of the manifest received from the user device to the second manifest hashed by the external system.

Another implementation of the present disclosure is a method including receiving, by a processing circuit, a request from a user device of a user to add the user to a trusted user service associated with a provider of goods or services, receiving, by the processing circuit, health behavior data of a health behavior data stream associated with behavior relating to a spread of an infectious disease at a physical location, determining, by the processing circuit, whether the user meets one or more health safety levels based on the health behavior data, adding, by the processing circuit, the user to the trusted user service in response to a determination that the user meets the one or more health safety levels, and generating, by the processing circuit, an access indication for access to the physical location at one or more particular times in response to the determination that the user meets the one or more health safety levels.

In some embodiments, the method includes adding, by the processing circuit, the user to a trusted shopper list of trusted shoppers in response to the determination that the user meets one or more health safety rules, receiving, by the processing circuit, second health behavior data associated with a second user of the trusted shopper list of trusted shoppers, determining, by the processing circuit, based on an analysis of the second heath behavior data, that the second user has broken one or more health safety rules, and removing, by the processing circuit, the second user from the trusted shopper list of trusted shoppers in response to a second determination that the second user has broken one or more health safety rules.

In some embodiments, the method includes receiving, by the processing circuit, a service provider request for a particular service provider of a list of trusted service providers from the user device, verifying, by the processing circuit, that the user of the user device has access to the list of trusted service providers, and providing, by the processing circuit, an indication of the particular service provider to the user device.

In some embodiments, receiving, by the processing circuit, risk data of a risk data stream indicating risk levels associated with the user. In some embodiments determining, by the processing circuit, whether the user meets one or more health safety levels includes correlating the health behavior data of the health behavior data stream with the risk data of the risk data stream.

In some embodiments, the risk data indicates at least one of disease infection levels of one or more geographic areas that the user has been present within during a particular period of time or contact of the user with one or more infected persons.

In some embodiments, the access indication is associated with access to the physical location at one or more restricted hours restricted for members of the trusted user service.

In some embodiments, the health behavior data is received from a surveillance system and is video data of the user at the physical location. In some embodiments, the method further includes determining, by the processing circuit, whether the health behavior data meets the one or more health safety levels by analyzing the video data to determine whether the user follows one or more health safety rules within the physical location.

In some embodiments, the one or more health safety rules include one or more social distancing guidelines, use of a mask, or use of sanitization within the physical location.

Another implementation of the present disclosure is a system including one or more memory devices having instructions stored thereon. The system includes one or more processors configured to execute the instructions to receive a request from a user device of a user to add the user to a trusted user service associated with a provider of goods or services, receive a travel history of the user indicating destinations that the user has traveled to, determine whether the user meets one or more health safety levels by analyzing the travel history of the user, add the user to the trusted user service in response to a determination that the user meets the one or more health safety levels, and generate an access indication for the user to access the physical location at one or more particular times in response to the determination that the user meets the one or more health safety levels.

In some embodiments, the instructions cause the one or more processors to add the user to a trusted shopper list of trusted shoppers in response to the determination that the user meets one or more health safety rules, receive second health behavior data associated with a second user of the trusted shopper list of trusted shoppers, determine, based on an analysis of the second heath behavior data, that the second user has broken the one or more health safety rules, and remove the second user from the trusted shopper list of trusted shoppers in response to a second determination that the second user has broken the one or more health safety rules.

In some embodiments, the personal risk data indicates whether the user has previously contracted and recovered from the infectious disease.

In some embodiments, the instructions cause the one or more processors to receive a manifest from a user device of the user representing a travel activity performed by the user, receive a second manifest from a blockchain, wherein the second manifest is a copy of the manifest, wherein the second manifest is stored in the blockchain by an external system to create a record of the travel activity performed by the user, and validate the manifest received from the user device with the second manifest of the blockchain.

In some embodiments, the second manifest includes a first signature of the user device and a second signature of the external system. In some embodiments, the instructions cause the one or more processors to determine that the first signature is authentic with a first public key of the user device and determine that the second signature is authentic with a second public key of the external system.

In some embodiments, the second manifest is hashed by the external system. In some embodiments, the instructions cause the one or more processors to validate the manifest received from the user device by determining that the manifest matches the second manifest by hashing the manifest received from the user device and comparing a hash of the manifest received from the user device to the second manifest hashed by the external system.

BRIEF DESCRIPTION OF THE DRAWINGS

Various objects, aspects, features, and advantages of the disclosure will become more apparent and better understood by referring to the detailed description taken in conjunction with the accompanying drawings, in which like reference characters identify corresponding elements throughout. In the drawings, like reference numbers generally indicate identical, functionally similar, and/or structurally similar elements.

DETAILED DESCRIPTION

Overview

Figure 1:
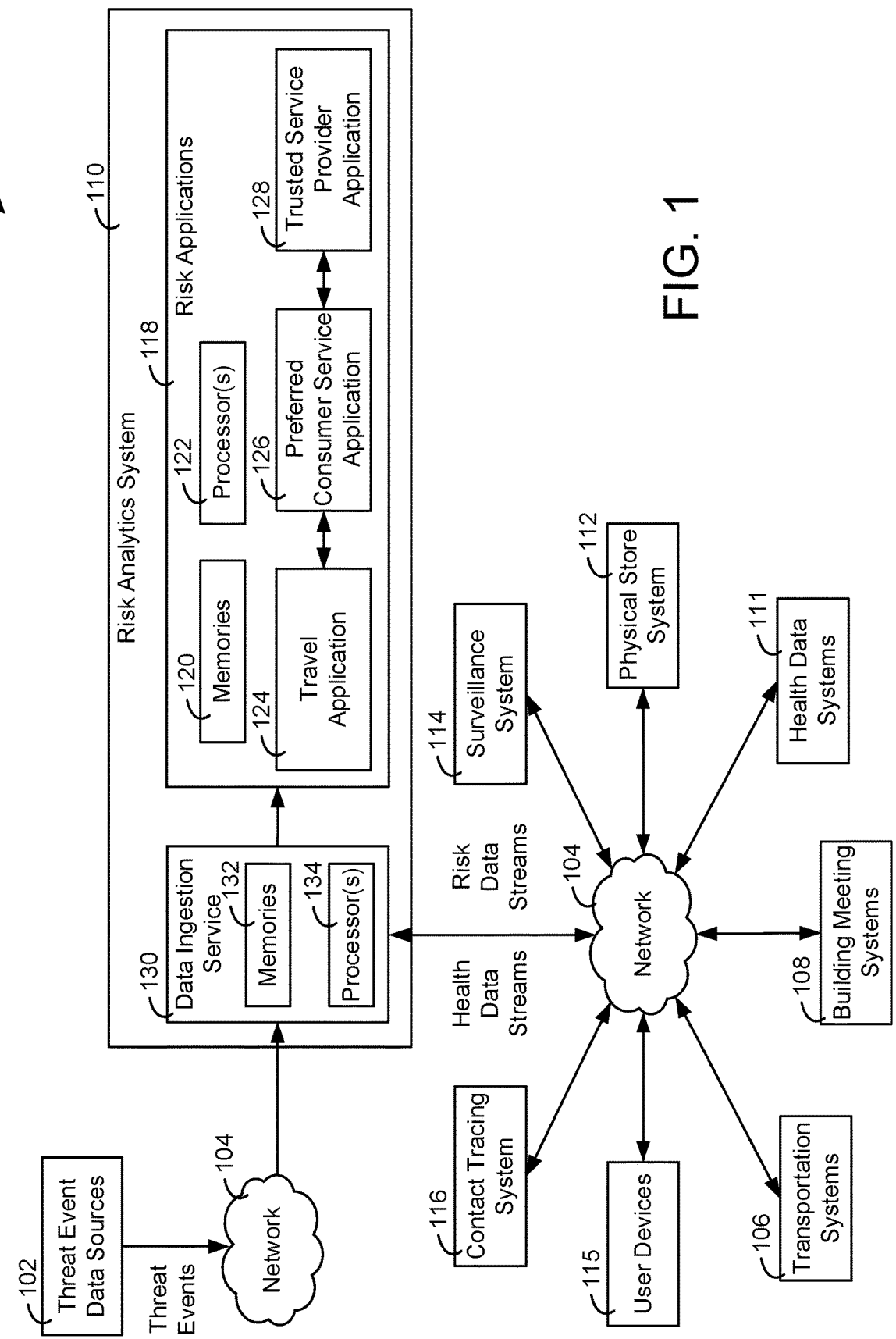
FIG. 1 is a block diagram of a system including a risk analytics system that receives health data streams and risk data streams for analyzing disease related risk including a travel application, a consumer service application, and a trusted service provider application, according to an exemplary embodiment.

Referring generally to the FIGURES, systems and methods are shown that operate based on disease related risk, according to various exemplary embodiments. First, the systems and methods described herein relate to dynamic travel planning based on disease related risk. The systems can generate an itinerary that plans a trip for a user in such a manner that the health of the user is taken into account with respect to disease related risks. For example, the systems can generate the itinerary to include plans that utilize transportation options, overnight accommodation options, and/or other travel decisions that pose a low risk level to the user. Furthermore, the itinerary can be updated dynamically by the system so that as factors affecting a risk level of the user change during the traveling of the user, suggested updates to the travel itinerary can be received and acted upon by the user.

The system can evaluate risk levels associated with the travel of the user while the user is traveling. This can result in an evolving indication of risk that is easily understandable by a user. Furthermore, because the system can cause user interfaces to display indicators such as the evolving risk and the suggested updates to the travel itinerary, a user can easily understand what actions the user can take to reduce the infection risk that the user is exposed to during their trip.

The systems and methods can further relate to managing a trusted service provider network based on disease related risk. The system can receive health related data streams associated with a particular service provider. For example, the health related data streams can indicate the social distancing, disinfection, and/or screening procedures that a service provider uses for their rental cars, hotel rooms, physical shopping stores, etc. Furthermore, the system can receive risk data of a risk data stream. The risk data can indicate risk levels associated with the service provider, for example, disease infection levels in a geographic area that the service provider operations, number of infected individuals that have visited a physical store or used a car or hotel room of the service provider, and/or any other risk related data.

Based on the health data streams and the risk data streams associated with the service provider, the system can determine whether to add or remove the service provider from a trusted service provider network. The system can correlate the health and risk data streams. This correlation can allow for a determination of risk levels of the service provider that allows for more accurate and granular insights into the risk of the service provider than would be identified from the health data stream or the risk data stream individually. By managing the trusted service provider network to include highly reliable service providers that follow protocols and pose a low risk to customer or business partners, other entities that wish to use a reliable service provider can consult the trusted service provider network to find a safe and reliable service provider. For example, a customer looking for a car rental service could query the trusted network of service providers to identify a safe car rental service.

Furthermore, the systems and methods described herein relate to a preferred consumer service application. The system can be configured to receive a request from a user to be added to a preferred consumer service to acquire benefits offered to members of the preferred consumer service, e.g., price discounts, access to restricted shopping times at a physical store, etc. The system can be configured to receive data of a health data stream associated with the user and risk data of a risk data stream associated with the user. Again, the correlation of health and risk data can uncover greater insight into risk levels associated with the user that would not be identified with the health or risk data individually.

The health data stream can indicate whether the user follows social distancing practices, disinfection and hand washing practices, mask wearing policies, etc. The risk data can be data of a risk data stream can indicate whether the user has come into contact with infected individuals, lives or works in a high infection geographic area, has recently visited a country with a high infection level, and/or any other risk factor. Based on the health data stream and the risk data stream, the systems and methods can add or remove users from the preferred consumer service.

Referring now to FIG. 1, a system 100 including a risk analytics system 110 that receives health data streams and risk data streams for analyzing disease related risk including a travel application 124, a preferred consumer service application 126, and a trusted service provider application 128 is shown, according to an exemplary embodiment. The risk analytics system 110 includes a data ingestion service 130 and risk application 118 that include the travel application 124, the preferred consumer service application 126, and the trusted service provider application 128.

The data ingestion service 130 can be configured to ingest health data of health data streams and risk data of risk data streams. Furthermore, the data ingestion service can ingest threat events. The ingested data can be provide to the risk application 118. The data ingestion service can include one or more memories 132 and one or more processors 134.

The processors 134 can be a general purpose or specific purpose processor, an application specific integrated circuit (ASIC), one or more field programmable gate arrays (FPGAs), a group of processing components, or other suitable processing components. The processors 134 may be configured to execute computer code and/or instructions stored in the memories 132 or received from other computer readable media (e.g., CDROM, network storage, a remote server, etc.).

The memories 132 can include one or more devices (e.g., memory units, memory devices, storage devices, etc.) for storing data and/or computer code for completing and/or facilitating the various processes described in the present disclosure. The memories 132 can include random access memory (RAM), read-only memory (ROM), hard drive storage, temporary storage, non-volatile memory, flash memory, optical memory, or any other suitable memory for storing software objects and/or computer instructions. The memories 132 can include database components, object code components, script components, or any other type of information structure for supporting the various activities and information structures described in the present disclosure. The memories 132 can be communicably connected to the processors 134 and can include computer code for executing (e.g., by the processors 134) one or more processes described herein.

The data ingestion service 130 can receive the threat events, the health data streams, and the risk data streams via network 104. The network 104 can communicatively couple the devices and systems of system 100. In some embodiments, the network 104 is at least one of and/or a combination of a Wi-Fi network, a wired Ethernet network, a ZigBee network, a Bluetooth network, and/or any other wireless network. The network 104 may be a local area network or a wide area network (e.g., the Internet, a building WAN, etc.) and may use a variety of communications protocols (e.g., BACnet, IP, LON, etc.). The network 104 may include routers, modems, servers, cell towers, satellites, and/or network switches. The network 104 may be a combination of wired and wireless networks.

The system 100 includes a contact tracing system 116, user devices 115, transportation systems 106, building meeting systems 108, health data systems 111, physical store system 112, surveillance system 114, and threat event data sources 102. The threat event data sources 102 can be data sources that provide a notification of a threat occurring. The threat event data sources 102 could be dataminr, NC4, Twitter, social media data, a news outlet, etc. The threat event data sources 102 can provide indications of threat events to the data ingestion service 130, for example, an indication of a disease outbreak, an indication of a protest occurring, an indication of a natural disaster, that a user has caught a disease, that a sporting event is occurring, etc.

The contact tracing system 116 can be a system or group of systems that monitor and track infected individuals and monitor and track other individuals who come into contact with the infected individuals. The contact tracing system 116 can be a centralized system that aggregates and stores data or a distributed system, e.g., multiple user devices running a local application. The contact tracing system 116 can be a user opt-in system where users allow for their location to be tracked and provide an indication to the contact tracing system 116 regarding whether they are experiencing disease symptoms, have been hospitalized due to a disease, and/or have tested positive for a disease.

In some embodiments, the contact tracing system 116 can be managed by the risk analytics system 110 or external to the contact tracing system 116. The contact tracing system 116 can be managed by another system, e.g., the contact tracing system 116 could be a Google contact tracing system or an Apple contact tracing system. The internal or external contact tracing could provide contact tracing data that the contact tracing system 116 is configured to use to generate risk scores for users and/or locations, in some embodiments. The contact tracing can be performed through peer to peer communication, e.g., ad-hoc communication between two user devices that identify an interaction between two users. In some embodiments, the contact tracing can be performed with badges that communicate with building scanning systems. In some embodiments, a the contact tracing system uses vehicle tracking data, e.g., GPS data of the vehicle and/or driver detection and/or identification.

The user devices 115 can be personal device of a user. For example, the user devices can be smart phones, laptops, tablets, etc. The user devices 115 can be carried by a user and configured by the user to provide location data indicating a location of a user device to the data ingestion service 130. The user devices 115 can include display devices, e.g., touch-screens, light emitting diode (LED) displays, organic light emitting diode (OLED) display, a liquid crystal display (LCD), etc. The user devices 115 can further include interface devices, e.g., capacitive or resistive touch inputs, keyboards, mouse, a remote, etc.

The transportation systems 106 can provide transportation data to the risk analytics system 110. The transportation systems 106 can be an airline system, a train system, a bus system, a taxi system, a car rental system, a ride share system, and/or any other type of system. For example, if the transportation system is an airline system, the airline system can provide risk data, e.g., data that indicates an increased risk of infection, such as an indication of flight lengths, layovers, distances between terminals and/or gates, number of booked passengers, etc. to the risk analytics system 110.

The building meeting systems 108 can be a system that books meeting rooms within a building and/or buildings. The building meeting systems 108 can provide the risk analytics system 110 with risk data regarding building meeting rooms of a building, e.g., room size, room ventilation rates, room capacity, time since the room was last occupied, etc. Furthermore the building meeting systems 108 can provide health data associated with the meeting rooms, room cleaning or disinfection frequency, time since last disinfection, etc.

The health data systems 111 can be systems that aggregate disease related infection levels for geographic areas (e.g., risk data streams) and provide the information to the risk analytics system 110. The health data systems 111 can be Center For Disease Control And Prevention (CDC) systems, data published by John Hopkins University systems, data published by the World Health Organization (WHO), and/or any other health data system. The data published by the health data system 100 can be real-time data that changes as disease infections are detected and reported by hospitals and/or disease testing facilities.

The physical store system 112 can be systems of a physical place of business, e.g., a retail store, a restaurant, a car rental facility, and/or any other type of physical brick and mortar store. The physical store system 112 can provide health related data, e.g., indications of social distancing practiced at the store, signs and instructions for customers to follow within the building (e.g., standing six feet apart, wearing a mask, etc.), indications of cleaning and disinfection practices, etc.

The surveillance system 114 can be a system of one or more cameras, video storage and/or analysis systems, etc. The surveillance system 114 can integrate with and/or communicate to the physical store system 112. The surveillance system 114 can be located at a building, e.g., a physical store. The surveillance system 114 can identify, based on captured video data, whether employees and/or customers follow social distancing practices, cleaning and/or disinfection practices, wear masks, etc.

The risk application 118 include the travel application 124, the preferred consumer service application 126, and the trusted service provider application 128. These application 124-128 can be executed by one or more processors 122 and stored on one or more memories 120. The one or more processors 122 can be the same as or similar to the one or more processors 134 while the one or more memories 120 can be the same as or similar to the memories 132.

The travel application 124 can be a system for planning travel for a user, an employee of a company, a subscribed individual, etc. The travel application 124 can be configured to generate and/or analyze travel plans based on real time risk to facilitate proper travel planning and/or mid-travel plan deviation. The travel application 124 can receive an indication of one or more destinations and time data from the user devices 115 and generate a travel itinerary (e.g., a data set including one or more selected transportation methods, one or more selected overnight stay reservations, one or more selected restaurants, etc.). In some embodiments, if a user authorizes data sharing, the travel application 124 can provide the travel itinerary to the contact tracing system 116 for the contact tracing system 116 to operate one or contact tracing purposes.

The travel application 124 can analyze the health data streams and/or risk data streams received from the network 104 to determine whether any deviations should be taken to the travel itinerary while the user is traveling. In some embodiments, the health data streams and/or the risk data streams are combined within a single data stream. For example, real-time risk related data or threat event data can indicate that a deviation in travel would lower a risk score of the user. For example, the travel application 124 could calculate a risk score associated with the user flying a particular airline through a particular airport, dining at a restaurant, and sleeping at a hotel.

However, if there is a disease outbreak associated with the restaurant while the user is on their flight, the travel application 124 could generate a suggested alternative restaurant for the user to dine in and cause a user interface of a user device to display the suggestion to be accepted or rejected by the user via one or more accept or reject interface elements displayed on the user interface. Furthermore, the travel application 124 could reschedule a meeting room from a first room to a second room in response to a detection that the first room has not been sanitized, an infected individual has recently been present in the first room, etc.

In some embodiments, the travel application 124 can score multiple routes of travel based on the mode of transportation and a destination. One or multiple routes and/or the score for each route can be provided to a user for review to select a route that is safest where it is unlikely that the user will catch an infectious disease. Each route can be scored based on the travel mode itself in addition to restaurants, hotels, rest stops, etc. along the route. The route with the lowest risk score or the highest safety score can be provided to the user. In some embodiments, the travel application 124 can recommend that the user skip having dinner at a certain hotel or in a certain city, stay in a hotel outside of a city with a high infection rate, skip visiting a city, etc. The travel application 124 can generate a travel itinerary based on multiple disparate factors, the travel mode itself (e.g., plane, train, bus, car), the hotels along the routes, the restaurants, along the routes, the infection levels of the various cities along the routes and/or the destinations, etc.

The preferred consumer service application 126 can manage a service that one or more users subscribe to, e.g., via the user devices 115. The service can be a subscription service that provides benefits to subscribed users, e.g., price discounts on products or service, access to restricted shopping hours in a physical store, exclusive product or service previews, early product or service access, etc. The access to the restricted shopping hours, or other access to an asset of a goods or service provider, could be a credential, a password or an identifier of the user. The preferred consumer service application 126 can receive health data streams and/or risk data streams associated with a user to determine whether the user should be added to the preferred consumer service and/or granted the discounts of the preferred consumer service.

For example, the surveillance system 114 can indicate whether the user has worn a mask when visiting a physical store, has practiced social distancing in the physical store, etc. and should be granted access to price discounts. Furthermore, the contact tracing system 116 can provide risk data that indicates whether the user has been in contact with infected individuals and should be provided access to the restricted shopping hours.

In some embodiments, the preferred consumer service application 126 can generate utilize a travel history (e.g., a collection of travel data, contact tracing data, hotel receipts, restaurant receipts, user reported data, etc.) of a user to determine whether to classify the user as a preferred consumer. In some embodiments, the preferred consumer service application 126 is configured to determine an expected risk level of a user of a planned trip to an actual risk level resulting from actual travel decisions made during the trip (e.g., what the user did during the trip, where the user traveled, where the user stayed, who the user came into contact with, etc.). Based on the difference between the expected risk level and the actual risk level, the preferred consumer service application 126 can determine whether the user should be added to, retained in, or removed from a preferred consumer list.

The trusted service provider application 128 can manage a network of trusted service providers based on health data streams and/or risk data streams associated with the trusted service providers. The application 128 can analyze data associated with the service provider, e.g., what disinfection practices are performed by the service provider for their store, rental cars, hotel rooms, etc. Whether the service provider is located in a high infection area or a low infection area (e.g., is located in a geographic area associated with an infection level above or below particular amounts), etc. If the trusted service provider meets one or more requirements as determined by the health data streams and the risk data streams, the trusted service provider can be added by the trusted service provider application 128 to a network of trusted service providers list. Partnering systems and/or consumer systems can query the trusted service provider application 128 for a trusted service provider and can be recommended a trusted service provider by the trusted service provider application 128.

In some embodiments, the trusted service provider application 128 scores a building or buildings of a service provider to determine whether to add the service provide to the trusted service provider application 128. The application 128 can generate a safety score associated with communities, buildings, etc. For example, the application 128 can be configured to generate a score for a building based on building sanitation practices, HVAC air handling practices, fire system practices, screening practices, etc.

In some embodiments, the applications 124-128 can communicate with each other to exchange data. For example, the travel data of users stored by the travel application 124 can be provided to the preferred consumer service application 126 to monitor user movement if the user has given approval for their movement to be tracked. Furthermore, the travel application 124 can make travel determinations based on whether transportation, hotels, car rental services, restaurants, etc. are trusted and safe as can be indicated by the trusted service provider application 128.

Furthermore, the risk application 118 can exchange data with the systems 106-116. This can form a community of companies, e.g., companies that are trusted services as identified by the trusted service provider application 128. This can create a group of partner companies and/or a consortium of companies. For example, travel data of the travel application 124 can be shared with the contact tracing system 116.

Figure 2:
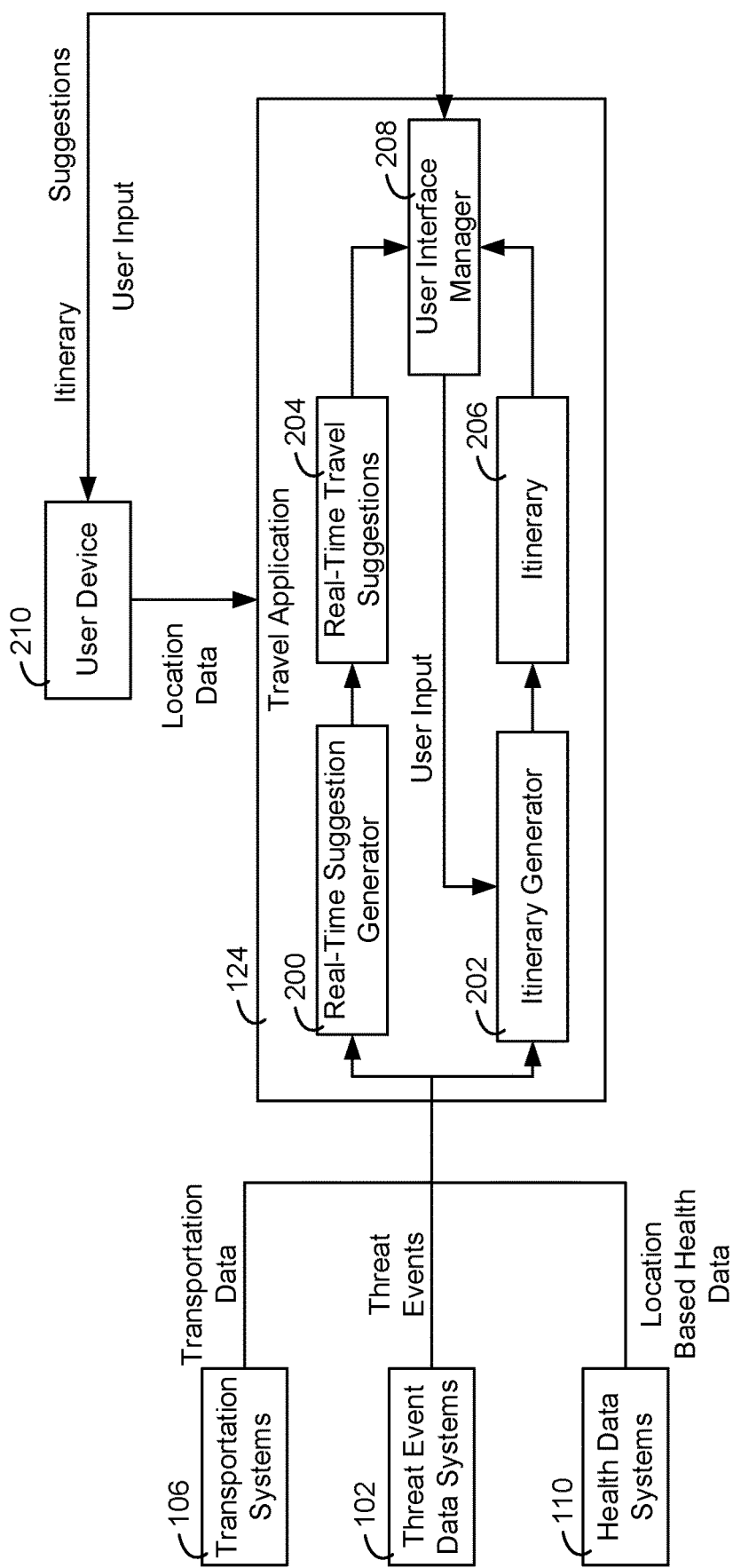
FIG. 2 is a block diagram of the travel application of FIG. 1 in greater detail, according to an exemplary embodiment.

Referring now to FIG. 2, the travel application 124 of FIG. 1 shown in greater detail, according to an exemplary embodiment. The travel application 124 can receive user input from a user device 210. The user device 210 can be one of, or similar to the user devices 115. The user device 210 can be a smartphone and can include a touchscreen for viewing data and/or providing input. A user can define one or more travel destinations, one or more travel dates and/or times, departure times, arrival times, food preferences, overnight stay accommodation preferences, etc. This data can be provided as the user input to the travel application 124.

An itinerary generator 202 of the travel application 124 can receive transportation data from the transportation systems, 106, threat events from the threat event data sources 102, and location based health data from the health data systems 111. The itinerary generator 202 can generate a travel itinerary 206 based on the destinations provided by the user and the data received from the systems 106-115. The itinerary generator 202 can analyze legs of a flight, legs of a travel plan, real time contact tracing of other people in an area, risk factors associated with varying layovers, length of layovers, distance between flight gates, likelihood of needing to eat, social distancing practice scores in airports, infection levels of various geographic locations, etc. to select transportation options for the itinerary 208.

The itinerary generator 202 can calculate a risk score associated with multiple possible transportation options and weight each score based on risk factors such as a number of stops since each stop increases contact risk, e.g., waiting in new lines with new people. Furthermore, for rideshare or car rental options, the length of the ride may be considered in risk that affects the risk score of the itineraries. Furthermore, an age of a user associated with the user device 210 and/or the presence of preexisting conditions can be considered by the itinerary generator 202 in generating the itinerary 206. Some users, e.g., young users without any preexisting health conditions, may have a higher risk tolerance than older users with preexisting health conditions.

In some embodiments, wherein the risk data is contact tracing data received from the contact tracing system 116. The contact tracing data indicates one or more past locations and one or more future planned locations of one or multiple different people infected by a disease. The itinerary generator 202 can be configured to generate the travel itinerary 206 to include one or more transportation selections, transportation routes, and/or hotel accommodations that avoid the one or more past locations and the one or more future locations of the person infected by the disease. This reduces a risk level of the traveling user. Furthermore, as new locations of infected individuals is received by the travel application 124, the real-time suggestion generator 200 can generate updates to the itinerary 206 that avoid the locations of the infected individuals, e.g., avoid getting on a plane that an infected individuals is on, avoid a hotel that a high number of infected individuals are staying at, etc.

Based on risk data associated with various dining options, the itinerary generator 202 can be configured to generate a risk value associated with each of the dining options and select a dining option with a lowest risk value and/or with a risk value less than a predefined amount. In some embodiments, the itinerary generator 202 can select the dining option based on a risk toleration level of a user and one or more dining preferences of the user. The risk data can indicate numbers of infections in a geographic area that the restaurant is located in, whether infected individuals have or will go to the restaurant, etc. As the risk data changes for the restaurants, the real-time suggestion generator 200 can generate real-time travel suggestions 204 that recommend different restaurants in response a risk level for a planned restaurant exceeds a particular level.

In some embodiments, the itinerary generator 202 can be configured to generate a risk value for each of multiple overnight stay accommodation options. The itinerary generator 202 can cause the itinerary 206 to include selected overnight stay accommodations that reflect risk values less than a particular amount. For example, the itinerary generator 202 can identify multiple price ranges for accommodation options in a desired geographic destination regions and rank the accommodation options in terms of risk. The risk data can indicate infection levels in the area that each accommodation is located, whether infected individuals have, are, or will be staying the accommodation, etc. Furthermore, health data such as disinfection policies of each accommodation can be taken into account by the itinerary generator 202. Furthermore, as the risk data changes for the accommodations, the real-time suggestion generator 200 can generate updates to the accommodations, e.g., replacement accommodations.

In some embodiments, the itinerary generator 202 can generate a travel plan that avoids stopping in, or traveling through, one or more high infection geographic areas. For example, based on the location based health data received from the health data systems 111, the itinerary generator 202 can identify what flights, busses, or trains that stop, transfer, or move through geographic areas associated with high risk. The itinerary generator 202 can generate a travel plan including transportation selections that avoid the geographic areas with infection levels above a particular amount and instead route transportation through low risk geographic areas, geographic areas that have a lower level of infection risk than the high risk geographic areas.

The real-time suggestion generator 200 can be configured to generate the real-time travel suggestions 204 during travel of the user associated with the user device 210. The real-time suggestion generator 200 can receive real-time risk data streams, e.g., from the systems 106-116 that indicates changes or developments in risk. The real-time travel suggestions 204 can indicate one or more changes to transportation, restaurants, hotels, etc. that mitigate or reduce risk levels for the itinerary 206 of the user associated with the user device 210.

For example, based on contact tracing data received from the contact tracing system 116, the real-time suggestion generator 200 can determine that the user will have an overlapping contact in an airport, on a plane, within a hotel within an infected person. To avoid making contact with the infected person or persons, the real-time suggestion generator 200 can recommend alternative transportation, restaurants, or overnight accommodations that avoid contact with individuals or reduce a number of infected individuals that the user associated with the user device 210 may come into contact with. The real-time suggestion generator 200 can be configured to predictive a level of separation from infected persons during travel to determine a risk score and, based on the risk score, generate the real-time travel suggestions 204.

In some embodiments, the real-time travel suggestions 204 are based on location data received from the user device 210 and the location based health data received from the health data systems 111. For example, if a user stops at a restaurant in a geographic area associated with high infection rates (e.g., there is a hospital blocks from the restaurants with a high number of hospitalized infected persons) which can be determined by the real-time suggestion generator 200 from the location data of the user device 210 and the location based health data of the health data systems 111, the real-time suggestion generator 200 can generate a suggestion to avoid the restaurant. In some embodiments, the real-time travel suggestions 204 are suggestions to adjust certain legs of travel, change a travel time (e.g., shift by a day or week), or utilize risk mitigation (e.g., use of a mast, sanitization, social distancing, etc.)

In some embodiments, the travel application 124 can receive a planned activity from the user device 210 and score the activity with a risk score. For example, the user may ask a question, "How risky is it to dine downtown in Chicago tonight?" and the travel application 124 can respond to the question by calculating a risk score for Chicago dining based on infection levels in the city, based on contact traces in an area, whether the user plans to dine indoors or outdoors, sanitizing scores for restaurants, ratings for social distancing practices, levels of law enforcement, predicted weather (e.g., whether indoor or outdoor seating will be available). The risk score for the activity can provide an indication of how risky planned behaviors are.

Figure 3:
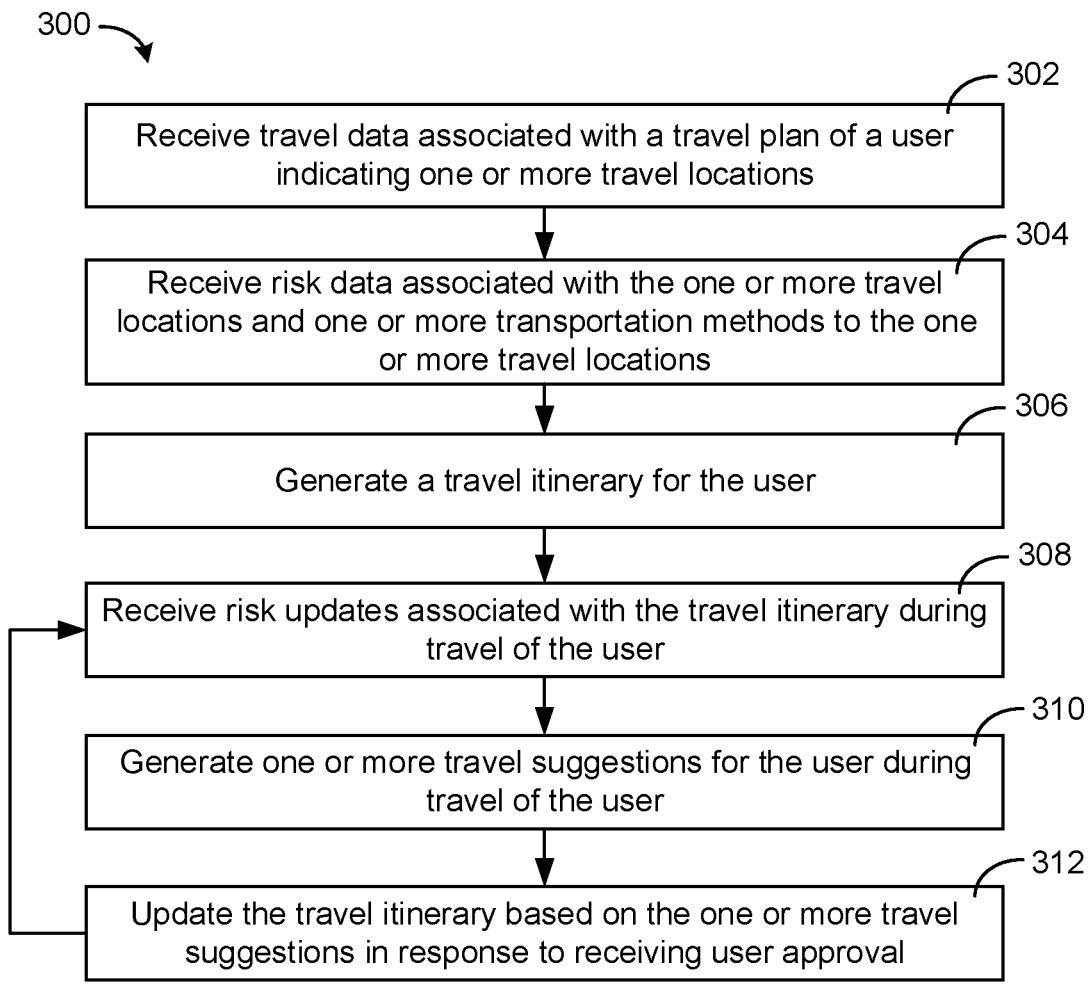
FIG. 3 is a flow diagram of a process of generating and dynamically updating a travel itinerary based on disease related risk that can be performed by the travel application of FIGS. 1-2, according to an exemplary embodiment.

Referring now to FIG. 3, a flow diagram of a process 300 of generating and dynamically updating a travel itinerary based on disease related risk that can be performed by the travel application 124 is shown, according to an exemplary embodiment. In some embodiments, the travel application 124 is configured to perform some or all of the steps of the process 300. In some embodiments, any computing device as described herein can be configured to perform the process 300.

In step 302, the travel application 124 can receive travel data associated with a travel plan of a user, the travel plan indicating one or more travel locations. The travel plan can indicate one or more destinations that the user will be visiting and approximate or definite times and/or days that the user needs to arrive in each destination. The travel plan can indicate preferred transportation options (e.g., rental car, airplane, bus, etc.), food preferences (e.g., vegan or vegetarian dining, preference for certain types of food, etc.), and/or any other travel preference of the user.

In step 304, the travel application 124 can receive risk data associated with one or more transportation methods to the one or more travel locations. For example, the travel application 124 can determine that a direct bus route from a first city to another city is less risky than a flight with multiple connections from the first city to the second city. The travel application 124 could select a first flight over a second flight in response to determining that infected individuals are booked for the second flight. Furthermore, the travel application 124 can select hotels and/or restaurants based on risk data associate with the hotels and restaurants.

In step 306, the travel application 124 generates the travel itinerary for the user. The travel itinerary can include one or more selected travel methods (e.g., a flight, a rental car, a bus, etc.), one or more restaurants, one or more over night stay accommodations, etc. In some embodiments, the user can review and edit the itinerary. Any changes the user makes to the itinerary can be associated with risk scores that the travel application 124 can provide to the user so that the user understands increases or decreases in risk associated with the actions. The user can accept the travel itinerary and the travel application 124 can book the travel methods, restaurants, and hotels for the user.

In some embodiments, the travel application 124 generates an infection travel risk score. The infection travel risk score can be displayed to a user via the user device 210 to provide a user with an indication of their travel risk. The infection travel risk score can be a value, level, or other indicator that indicates a risk associated with catching a disease. The infection travel risk score can be generated based on risk data indicating levels of risk associated with travel destinations of the user. The risk data can indicate infection levels associated with the travel destinations, population levels of the destinations, disease prevention practices performed at the destinations (e.g., lockdowns, use of masks, etc.), etc. Based on the risk destination risk data, the travel application 124 can generate the travel risk score.

Furthermore, in addition to, or instead of generating the travel risk score based on the destination risk data, the travel application 124 can generate the travel risk score based on personal risk data associated with the user. The personal risk data can indicate a risk associated with the user of the user device 210. The personal risk data can indicate the age of the user, the body mass index (BMI) of the user, medical conditions of the user (e.g., asthma, heart related problems), and/or activities performed by the user (e.g., whether the user frequently exercises, smokes, adheres to a vegan or vegetarian diet, consumes alcohol, etc.). In this regard, the travel risk score may be higher for a user that has asthma and is older than a particular age. In comparison, an infection travel risk scores of a user that exercises frequently and is younger than the particular age may have a lower risk score.

In some embodiments, the infection travel risk score changes overtime as data is collected. The travel application 124 can generate suggestions to update the travel plan of the user based on change in the infection risk score. For example, if the infection travel risk score increases to a value greater than a particular amount caused by change in the destination risk data or the personal risk data, the travel application 124 can generate a suggested update to the travel plan.

In some embodiments, the travel application 124 can generate multiple different travel routes from a travel plan of a user indicating an originating location and one or more travel destinations. The travel application 124 can score each route with an infection route risk score indicating the level of risk that a user experiences when traveling on the route. The infection route risk score can indicate infection risk levels associated with each travel route and/or personal risk data associated with the user. The travel application 124 can generate a suggestion to travel on one route of the routes associated with a lowest infection route risk score, can generate a user interface indicating each travel route and the score of each route, and/or can generate a list of the routes sorted in order of lowest risk score to highest risk score.

In step 308, the travel application 124 can receive risk updates associated with the travel itinerary during travel by the user. The updates may be threat events such as the rapid spread of a disease in a geographic area, an indication that an infected user has booked a hotel room in a hotel that the user is staying in, and/or any other update to risk levels associated with the itinerary of the user.

In step 310, the travel application 124 can generate one or more travel suggestions for the user that mitigate or reduce the risk updates. For example, if the user plans to stop at a restaurant in a geographic area that has greatly increased in infection levels, the suggestion could be to dine in a geographic area with a lower infection level. Similarly, if a flight is cancelled and a user will need to dwell in an airport for an extended period of time, the suggestion may be to take a direct bus to the destination instead of waiting in the airport. In step 312, the travel application 124 can update the travel itinerary based on the one or more suggestions in response to receiving user approval of the changes.

In some embodiments, at the end of the trip performed by the user, the travel application 124 can generate a summary page. The summary page can indicate an original risk score for the tip of the user generated by the travel application 124 and a concluding risk score based on deviations that the user has performed. For example, the concluding risk score can indicate what a user has done while traveling, where they have stayed, where they have eaten, and/or what other people the user has come into contact with.

Figure 4:
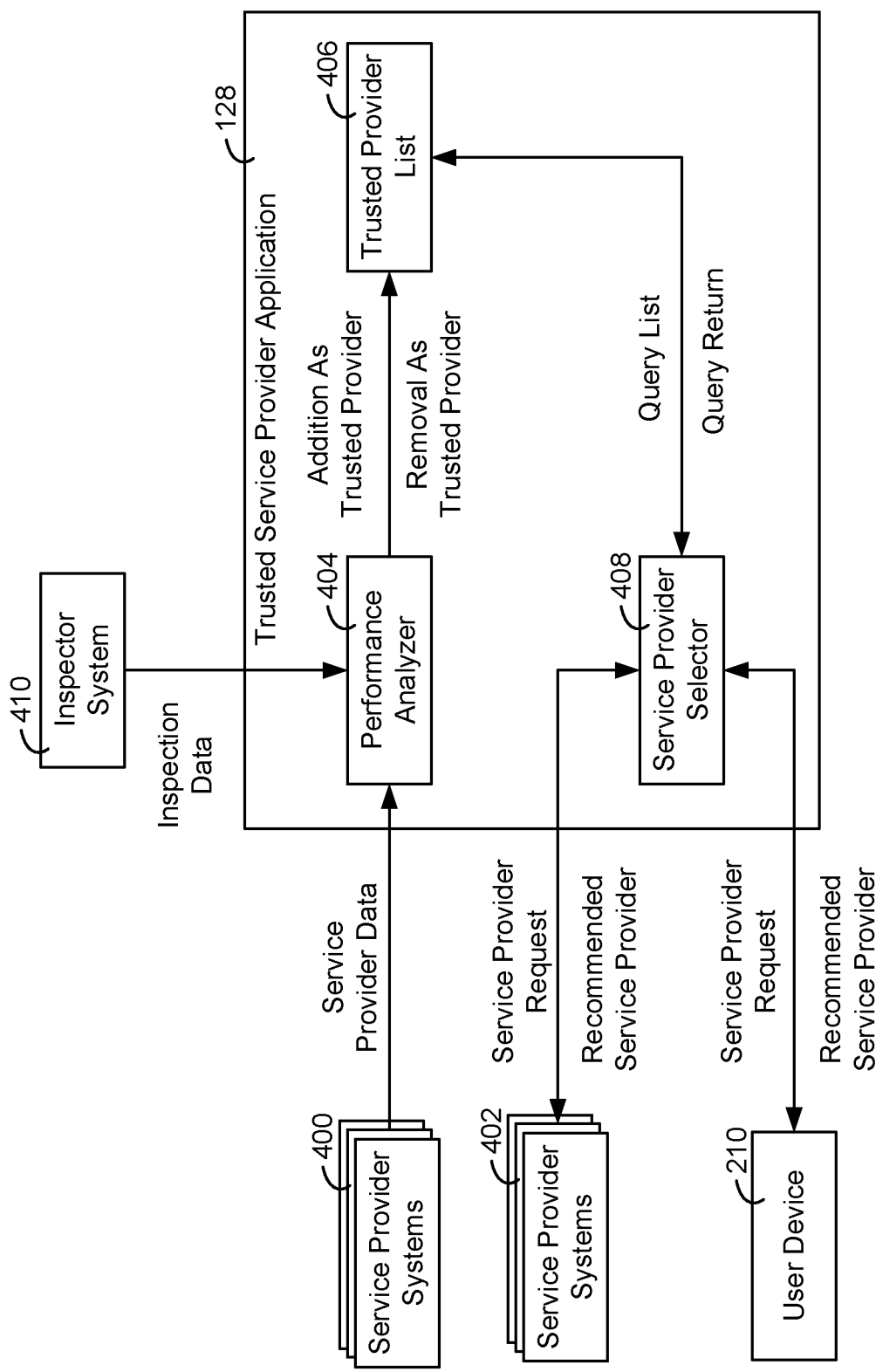
FIG. 4 is a block diagram of the trusted service provider application of FIG. 1 in greater detail, according to an exemplary embodiment.

Referring now to FIG. 4, the trusted service provider application 128 is shown in greater detail, according to an exemplary embodiment. The trusted service provider application 128 can communicate with service provider systems 400 and 402. The service provider systems 400 and 402 can be retail businesses, car rental businesses, airlines, airports, bus companies, restaurants, catering companies, and/or any other type of service provider. The trusted service provider application 128 can receive service provider data from the service provider systems 400.

The service provider data can be data of a health data stream associated with the service provider systems 400 and/or risk data streams. For example, the service provider data could indicate whether one or more social distancing practices, disinfection practices, and/or any other health related practices are performed by the service provider systems 400 to reduce the risk of spreading disease. The risk related data can be an indication of infection levels for geographic areas that stores of the service provider are located, numbers of infected individuals frequenting the stores, and/or any other risk related data.

The performance analyzer 404 can be configured to analyze the service provider data, e.g., correlate the health data streams and the risk data streams, to determine whether the service provider systems 400 are trusted or are not trusted. Trusted service provider systems can be added or maintained in a trusted provider list 406 while service providers that are not trusted can be removed from the trusted provider list 406. Furthermore, in some embodiments, the performance analyzer 404 can analyze the health data indicating health practices by each of the service provider systems 400. Inspection data received form an inspector system 410 can confirm that the health practices that the service provider systems 400 claims to practice are actually practiced.

For example, a hotel might score each room that people have stayed within based on contact tracing data, temperature measurements, and/or a survey. Each room could be rated based on risk and only low risk rooms rented out to individuals. In some embodiments, a heat map view could be provided by the hotel to users to determine whether or not to book room sin the hotel and/or what rooms that user would like to book. Based on these health practices, the performance analyzer 404 can determine that the hotel is a trusted service and can add the hotel to the trusted provider list 406.

The trusted service providers of the trusted provider list 406 can be configured to share disease related information with each other, facilitate contact tracing, etc. Furthermore, since the service providers of the trusted provider list may all perform health related tests for employees, sanitization of their physical stores, etc., other service providers may likely wish to do business with the service providers since they have been verified as being low health risk businesses. For example, a car service that rents cars can rate each car with a health risk score. If a service provider of the trusted provider list 406 wishes to rent cars from the service provider, as part of the trusted provider list 406, the car service may rent the service provider low risk score cars.

The service provider systems 402 and/or the user device 210 may access the trusted provider list 406 if the service provider systems 402 and/or the user of the user device 210 are subscribed to the trusted provider list 406. The service provide selector 408 can receive a query from the service provider systems 402 and/or the user device 210 for a recommended service provider. For example, the query could request recommended hotels or recommended airlines. The service provider selector 408 can query the trusted provider list 406 and return the recommended service provider to the service provider systems 402 and/or the user device 210. The service provider systems 402 may consult the trusted provider list 406 to help identify business partners while the user device 210 may consult the list to identify a service provider to purchase a product or service from.

In some embodiments, service providers of the trusted provider list 406 share risk data with each other. The risk data could be the health data streams or the risk data streams described with reference to FIG. 1 and elsewhere herein. The risk data can indicate the precautions or risks associated with assets of the service providers, e.g., what types of cleaning or health policies are performed at a physical store, whether infected individuals have visited physical sites, rented cars, stayed in hotel rooms, etc. In some cases, one service provider of the trusted provider list 406 can provide a request for risk data for another service provider of the trusted provider list 406 to the application 128. The application 128 can determine whether the one service provider has access to the risk data of the other service provider and response to the one service provider with the risk data in response to determining that the one service provider has access to the other service provider. In some embodiments, the trusted provider list 406 indicates one or more services providers that each service provider does and does not have risk data access for.

In some embodiments, the risk data that the services providers share indicate risk levels associated with assets of each service provider. For example, the risk level associated with a hotel room, a physical brick and mortar store, a conference room, a rental car, etc. In this regard, one service provider would have the data to make decisions such as reserve the safest hotel rooms, the safest conference rooms, visit the safest physical brick and mortar stores, etc.

Figure 5:
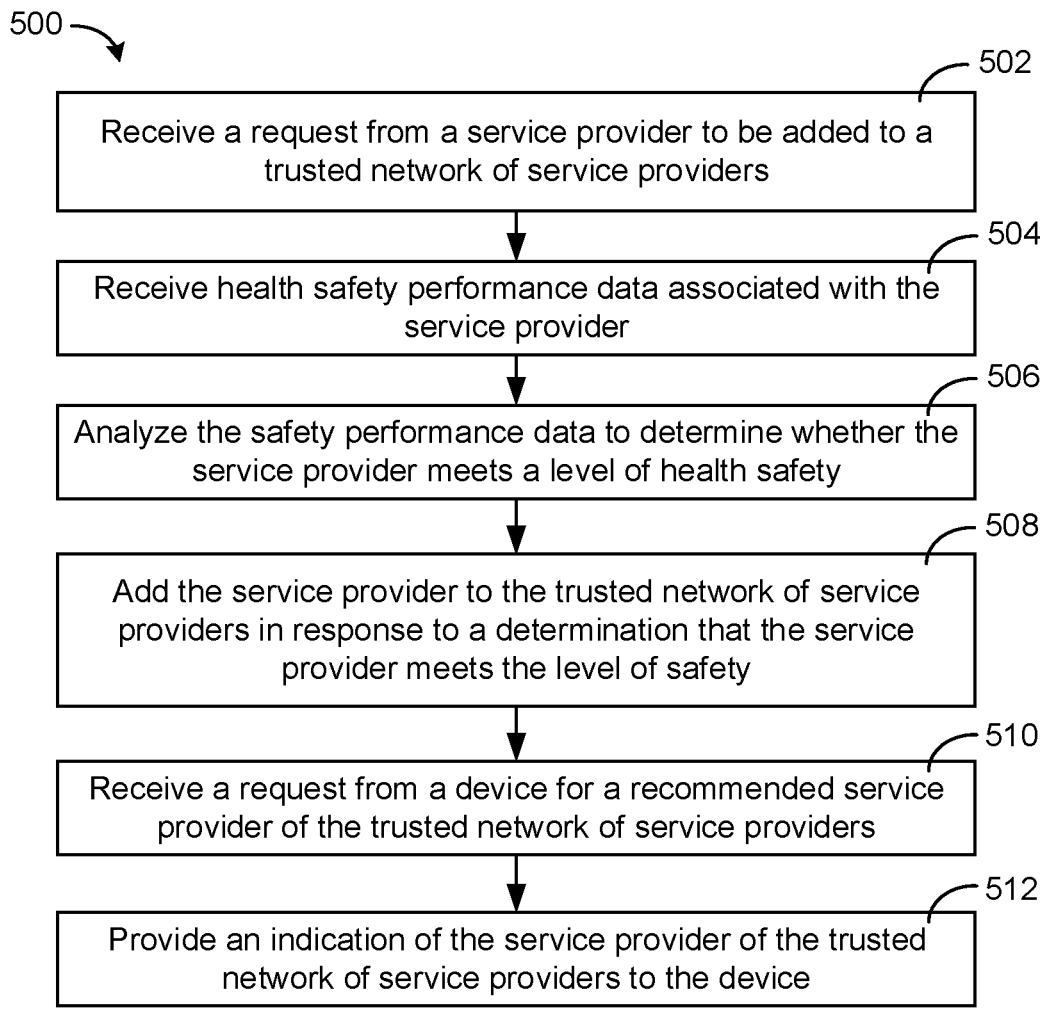
FIG. 5 is a flow diagram of a process of managing a trusted network of service providers based on disease related risk that can be performed by the trusted service provider application of FIGS. 1 and 4, according to an exemplary embodiment.

Referring now to FIG. 5, a process 500 of managing a trusted network of service providers based on disease related risk that can be performed by the trusted service provider application 128 is shown, according to an exemplary embodiment. In some embodiments, the trusted service provider application 128 is configured to perform some or all of the steps of the process 500. In some embodiments, any computing device as described herein can be configured to perform the process 500.

In step 502, the trusted service provider application 128 receives a request from a service provider system to be added to a trusted network of service providers. The service provider may be an airline, a hotel chain, a hotel location, an airport, a retail store, a retail chain, etc.

In step 504, the trusted service provider application 128 can receive health safety performance data associated with the service provider. The health safety performance data can include health data of a health data stream and risk data of a risk data stream. The health data can indicate performance of the service provider with respect to practicing social distancing, disinfection practices performed by the service provider, employee health testing, etc. The risk data can indicate whether the service provider is located in a high infection area, whether the service provider has been frequented by infected individuals, etc.

The health data and the risk data can be included within, or otherwise indicated by, a manifest. The manifest can be the manifest described with reference to FIGS. 13-14 and can be stored by the service provider. The trusted service provider application 128 is configured to validate the manifest received from the service provider, in some embodiments, based on another copy of the manifest stored in a blockchain and created by an external system. The trusted service provider application 128 can verify a hashed copy of the manifest stored in the blockchain, verify signatures of the service provider and/or the external system, etc. as described with reference to FIGS. 13-14.

In step 506, the trusted service provider application 128 can analyze the safety performance data to determine whether the service provider meets a level of health safety. The trusted service provider application 128 can correlate the health data of the health data stream with the risk data of the risk data stream to determine whether the service provider meets the level of safety. In step 508, in response to a determination that the service provider meets the safety level, the trusted service provider application 128 can add the service provider to the trusted network of service providers.

In step 510, the trusted service provider application 128 can receive a request from a device for a recommended service provider of the trusted network of service providers. For example, the device may be a user device of a user that wishes to purchase a product or service from a trusted service provider. In some embodiments, the device is a device of another service provider that would like to partner with a trusted service provider of the trusted service provider network. In step 512, in response to receiving the request, the trusted service provider application 128 can provide an indication of the service provider of the trusted network of service providers to the device.

Figure 6:
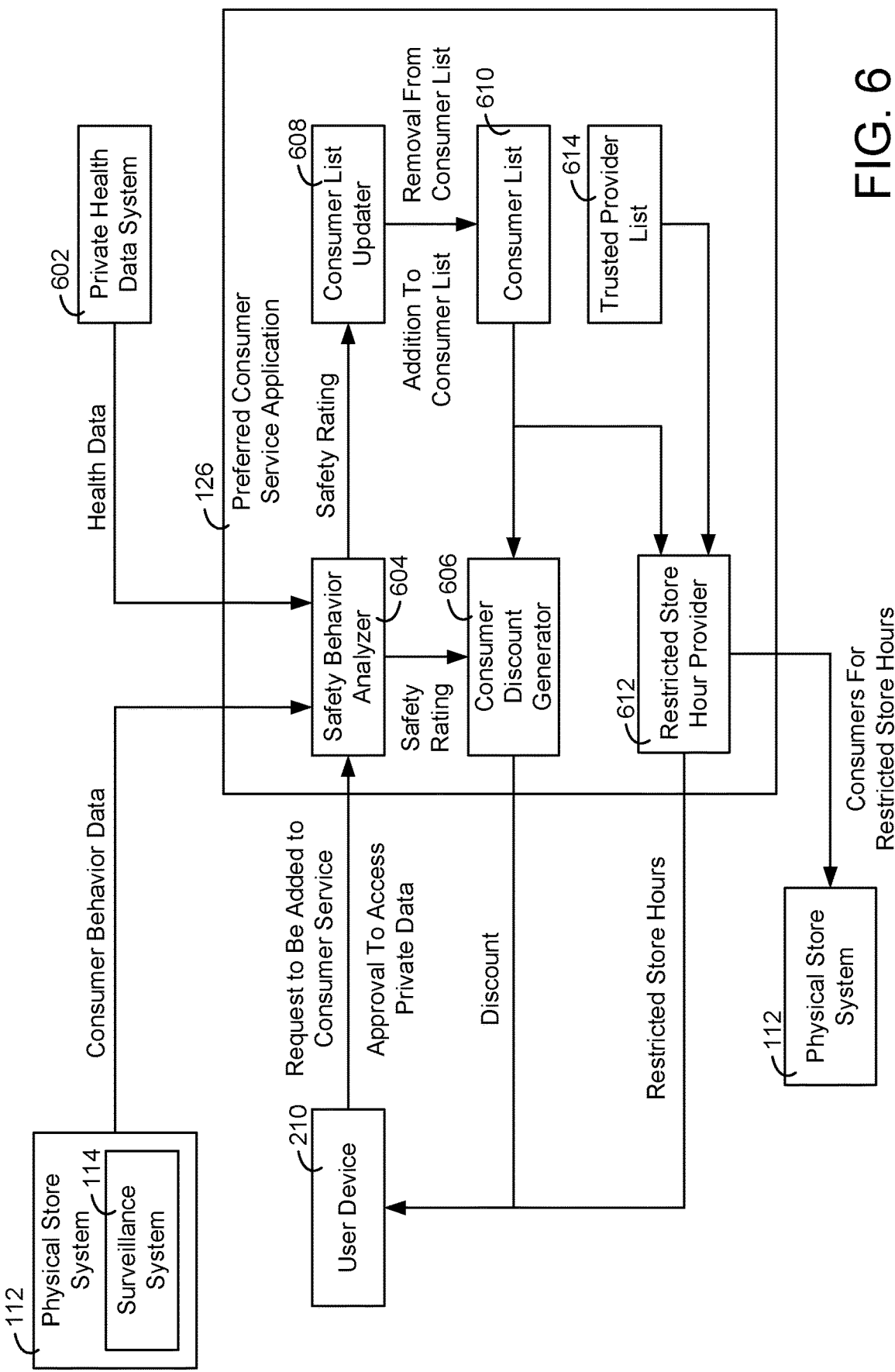
FIG. 6 is a block diagram of the consumer service application of FIG. 1 in greater detail, according to an exemplary embodiment.

Referring now to FIG. 6, the preferred consumer service application 126 is shown in greater detail, according to an exemplary embodiment. The preferred consumer service application 126 can be an opt-in application that a user subscribes to. The preferred consumer service application 126 can offer users dynamic pricing and/or access to the service providers of the trusted provider list 406. In some embodiments, the preferred consumer service application 126 is subscribed to by a user for a family. The preferred consumer service application 126 can provide a family member, or all family members, with risk data for each family member, real-time tracking, and/or risk levels for each family member.

The user device 210 can provide a request to be added to the consumer service and approval to access private data associated with the user of the user device 210 to the preferred consumer service application 126. A safety behavior analyzer 604 can receive consumer behavior data from a physical store system 112. The consumer behavior data can further be received from any of the systems 106-116. In some embodiments, the consumer behavior data is consumer data of a surveillance system 114 that indicates actions performed by a user within a physical store, e.g., wearing a mask, practicing social distancing, disinfecting, etc. Furthermore, the safety behavior analyzer 604 can receive health data associated with the user from a private health data system 602. The health data indicates whether the user has tested positive or negative for a disease, a recent body temperature measurement, etc.

The safety behavior analyzer 604 can analyze the consumer behavior, the health data, and/or various streams of risk data to determine a safety rating for the user. The risk data may indicate what geographic areas the user has visited and what infection levels are associated with those geographic areas, whether the user has come into contact with infected individuals, etc. The risk score can be provided to the consumer list updater 608. The consumer list updater 608 can add the user to the consumer list 610 and/or remove the consumer from the consumer list 610 based on the safety rating. If the safety rating is above a particular amount, the user can be added to the consumer list 610. If the safety rating is less than the particular amount, the user can be withheld from or removed from the consumer list 610.

Users of the consumer list 610 who may practice social distancing within a store, the user can be award a price discount for a product or service. The consumer discount generator 606 can generate a price discount for the user and provide the discount to the user device 210. Furthermore, if the user has been added to the consumer list 610, the user may have access to restricted store hours. The restricted store hour provider 612 can provide restricted store hours of the trusted provider list 614 to the user device 210. In some embodiments, the restricted store hour provider 612 can provide an identify or a credential of the user that has access to the restricted store hours to the physical store system 112 for automatic access to the physical store during restricted store hours.

Figure 7:
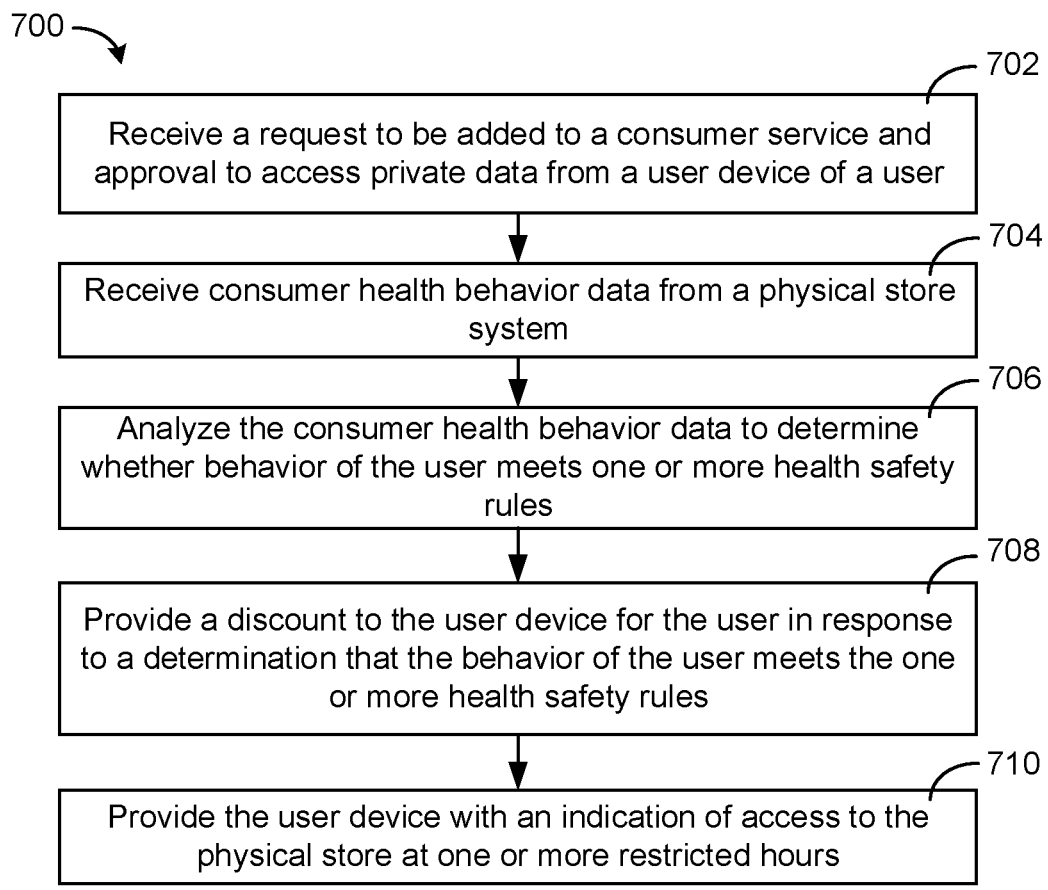
FIG. 7 is a flow diagram of a process of managing a trusted consumer service based on disease related risk that can be performed by the consumer service application of FIGS. 1 and 6, according to an exemplary embodiment.

Referring now to FIG. 7, a process 700 of managing a trusted consumer service based on disease related risk that can be performed by the preferred consumer service application 126, according to an exemplary embodiment. In some embodiments, the trusted service provider application 128 is configured to perform some or all of the steps of the process 700. In some embodiments, any computing device as described herein can be configured to perform the process 700.

In step 702, the preferred consumer service application 126 receives a request to be added to a consumer service and approval to access private date from a user device of a user. The user, in some embodiments, may provide payment information to subscribe themselves, and/or their family members to the consumer service.

In step 704, the preferred consumer service application 126 can receive consumer health behavior data from a physical store system. The consumer health behavior data may be data of a health data stream that indicates the precautions that the user is taking within the physical store, e.g., social distancing, opting in to contact tracing, using disinfection, wearing a mask, etc. The health behavior data can be a written survey that a user fills out to indicate what precautions the user has or is taking to avoid contracting or spreading a disease. Furthermore, the health behavior data could be video surveillance data indicating that the user has or is taking precautions to avoid contracting or spreading a disease in a physical store of a service provider.

In step 706, based on the consumer health behavior data, the preferred consumer service application 126 can determine whether the behavior of the user meets one or more health safety rules. Furthermore, the preferred consumer service application 126 can receive risk data associated with the user. The risk data may indicate whether the user has recently been located in high infection geographic areas, has opted into a trusted traveler program that tracks activity of a user, has come into contact with infected individuals, etc. The preferred consumer service application 126 can correlate the risk data stream with the health data stream to determine whether the user poses a health risk to the physical building.

In some embodiments, the consumer health behavior data is travel history data of a user. For example, the travel history may indicate one or multiple geographic locations that the user has been present at, one or multiple restaurants that the user has eaten at, and/or one or more hotels that the user has stayed at, etc. The analysis to determine whether the user should be added to a trusted consumer list and/or determine whether the user meets the one or more health safety rules can be performed based on the travel history data. The analysis can include determining a risk level for a user and comparing the risk level to a threshold by the travel application 124.

In some embodiments, the travel history data can be stored in a manifest of the user device and can be validated based on a copy of the manifest stored in the blockchain. In this regard, the preferred consumer service application 126 can be configured to receive the manifest from the user device and validate the manifest based on a hashed copy of the manifest stored in the blockchain. The consumer service application 126 can verify a signature of the manifest of the user device and/or an external system that records the activity of the user. The verification of the manifest is described in greater detail with reference to FIGS. 13-14.

In step 708, in response to determining that the behavior of the user meets the one or more health safety rules, the preferred consumer service application 126 can provide a discount to the user device for the user. The discount can incentive the user to continue practicing social distancing techniques while in the physical store, wearing a mask, etc. Furthermore, in step 710, the preferred consumer service application 126 can provide the user via the user device with access to the physical store at one or more restricted hours. The restricted hours may be hours only available to users that have a risk score less than a particular amount.

Figure 8:
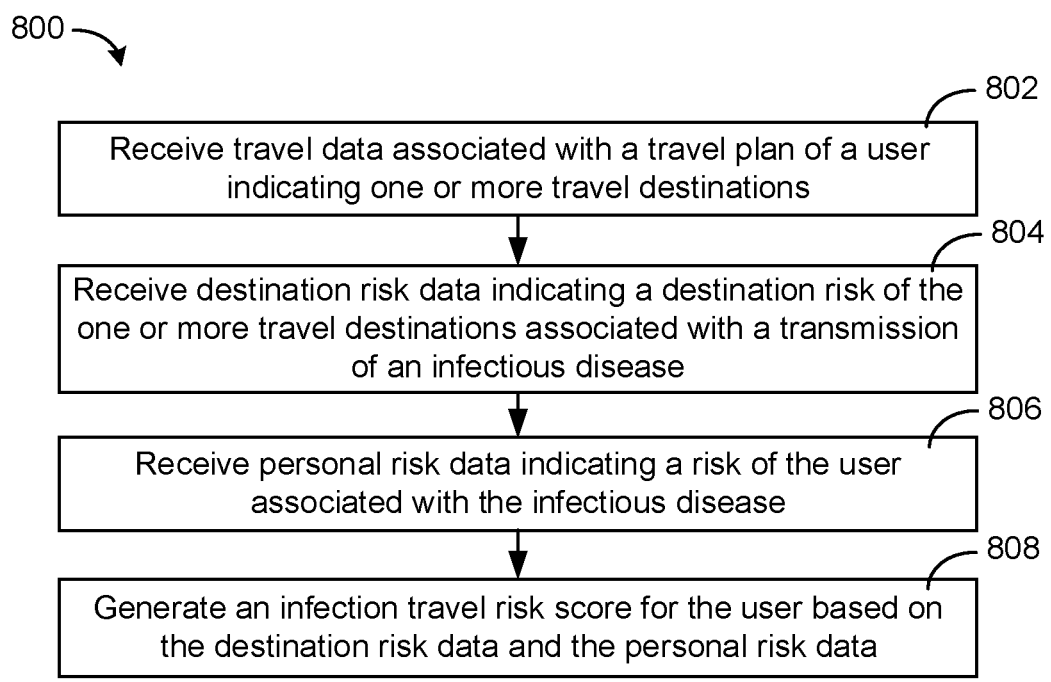
FIG. 8 is a flow diagram of a process of generating an infection travel risk score for a user by the travel application of FIG. 1, according to an exemplary embodiment.

Referring now to FIG. 8, a process 800 of generating an infection travel risk score for a user by the travel application 124 is shown, according to an exemplary embodiment. In some embodiments, the travel application 124 is configured to perform some or all of the steps of the process 800. In some embodiments, any computing device as described herein can be configured to perform the process 800.

In step 802, the travel application 124 receives travel data for a travel plan of a user indicating one or more travel destinations. The travel data can indicate a departure location, a departure time, a destination, and/or a destination time. The travel data can further include travel preferences, e.g., flight times (e.g., morning flights vs. red eye flights), preferred modes of travel (e.g., preference for using a bus), and/or any other indication of travel. The travel data can indicate a single travel destination or a sequence of travel destinations that a user plans on visiting, e.g., a set of cities that the user is traveling to for a vacation and/or a business trip.

In step 804, the travel application 124 receives destination risk data indicating a destination risk of one or more travel destinations associated with a transmission of an infectious disease. For example, the destination risk data can indicate a level of risk that a user may experience in a particular geographic area. For example, when the destination is a particular city, the city may have particular percentage of infected individuals that are infected with the infectious disease. The higher number of infected individuals, and/or a higher the rate of increase in the number of infected individuals, can indicate risk data for the destination.

In some embodiments, the destination is a particular hotel, a particular business campus, etc. The destination risk data can indicate the number of infected individuals at the destination. In some embodiments, the destination risk data can indicate a time since which an infected individual was last at the destination.

In step 806, the travel application 124 receives personal risk data indicating a risk of the user associated with the infectious disease. For example, the personal risk data can indicate characteristics of a user that is traveling. For example, the health of the user, the age of the user, and/or other information of the user. For example, the personal risk data could indicate health conditions of the user, e.g., whether the user has asthma, whether the user has a heart problem, whether the user has had a stroke, etc. The personal risk data can further indicate whether the user exercises frequently, has had a medical checkup recently, etc. The personal risk data can indicate whether the user is immune to a disease. For example, the personal risk data could indicate the results of an antibody test indicating that the user has previously caught and recovered from a disease. This can indicate that the user is immune to catching the disease.

In step 808, the travel application 124 can generate an infection travel risk score for the user based on the destination risk data received in the step 804 and/or the personal risk data received in the step 806. The travel application 124 can weigh the personal risk data against the destination risk data. For example, the travel application 124 can generate a higher infection travel risk score for the user when the user is susceptible to an infectious disease. For example, for a user that is at a particular age susceptible to a disease, the infection travel risk score can be set to a high value in response to the user traveling to, or being present, at a destination or location where an infected individual has recently been present.

Figure 9:
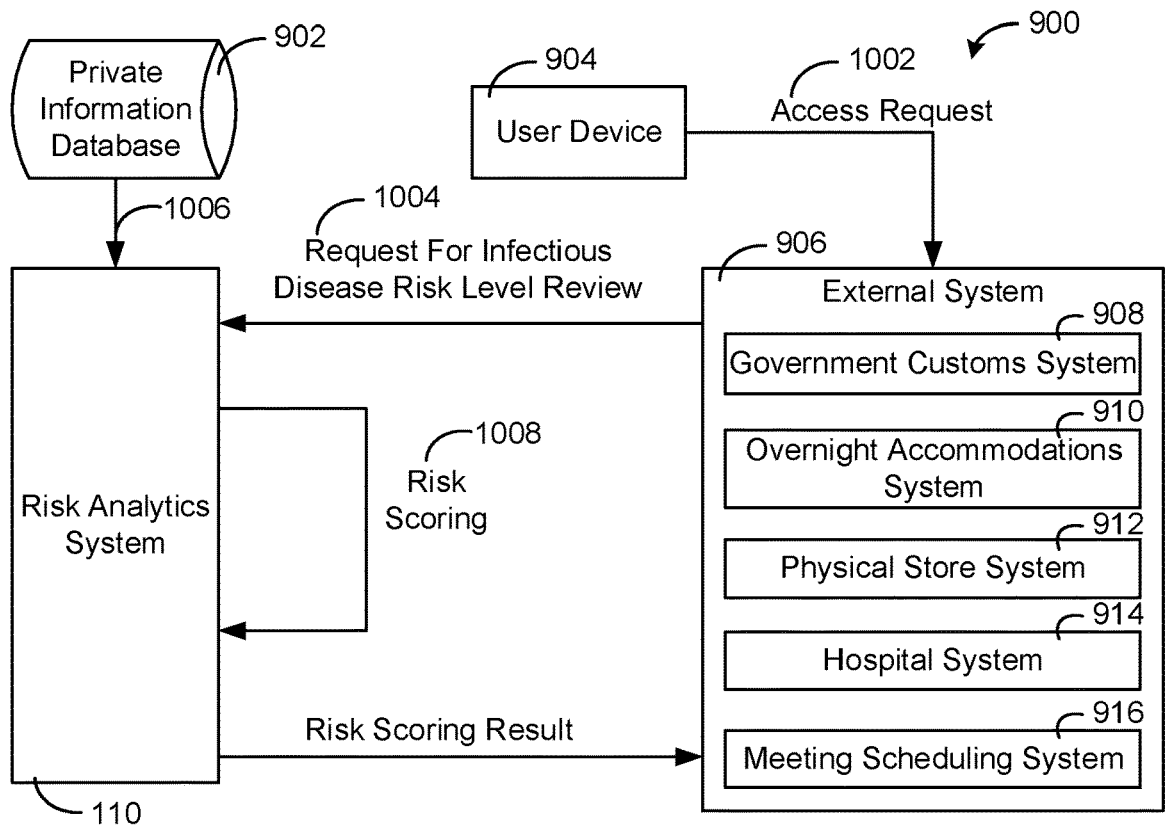
FIG. 9 is a block diagram of the risk analytics system of FIG. 1 performing risk scoring for an external system, according to an exemplary embodiment.

Referring now to FIG. 9, a system 900 of the risk analytics system 110 performing risk scoring for an external system 906 is shown, according to an exemplary embodiment. The system 900 includes a private information database 902, a user device 904, an external system 906, and the risk analytics system 110. The private information database 902 can be a database of disease risk related data, e.g., the health data streams, the risk data streams, antibody data of a user, infection travel risk scores (e.g., as determined by the travel application 124) and/or the threat events described with reference to FIG. 1. The private information database 902 can be any type of database, e.g., a private or public blockchain database (e.g., as described with reference to FIGS. 13-14), a Structured Query Language (SQL) database, a Relational Database Management System (RDMS) database, a relational database, a non-SQL (NoSQL) database, a non-relational database, etc.

The external system 906 can be a system external to the risk analytics system 110. For example, the external system 906 can be managed by a third party entity separate from the risk analytics system 110. The external system 906 can be a government customs system 908. The user device 904 may send an access request to the government customs system 908. In response to the access request, the government customs system 908 can request an infectious disease risk level for the user of the user device 904 and receive a risk scoring result from the risk analytics system 110. The government customs system 908, which may be a domestic or international system, can use the score to determine whether to grant the user entry into a country or location within a country. The score can be a credential, a trusted passport, and/or e-passport indicating that the user does not pose a threat to the country and/or the location within the country.

For example, if one country is blocking entry of travelers from another country, the first country could use the risk scoring to make exceptions for travelers from the second country if the travelers are scored at a low risk score, a risk score less than a particular amount indicating that the user poses a low risk of brining an infectious disease into the country. Various governments, government agencies (e.g., military, customs, etc.) can use the risk scoring provided by the risk analytics system 110.

In some embodiments, the external system 906 includes an overnight accommodations system 910, a physical store system 912, a hospital system 914, and/or a meeting scheduling system 916. The systems 910-916 could communicate with the risk analytics system 110 to determine risk scores that can be used to determine whether a user should have access to an overnight accommodation, access to shopping at a physical store, entry into a hospital, determine whether an employee can work on premises instead of remotely and/or can attend a meeting in person or should alternatively attend the meeting online. For example, if a user has recently traveled to a risky location, a location with a high infection count, the user may be asked to attend a meeting remotely or quarantine before returning to work in an office by the meeting scheduling system 916 communicating with the user device 904.

Instead of exposing the private information of the user of the user device 904 stored in the private information database 902, the risk analytics system 110 can act as a clearing house that validates threshold risk scores without exposing private information. The risk scoring result can be a numerical value of risk for a user and/or a pass fail binary value. In some embodiments, the request for infectious disease risk level review by the external system 906 includes a set of criterion of the external system 906. The risk analytics system 110 can be configured to query the private information of the user from the private information database 902 and determine whether the user meets the criterion. The risk analytics system 110 can return the score and/or a binary result of the analysis.

The risk analytics system 110 can be configured to score the private data of the user to determine a risk score of the user. The risk analytics system 110 can be configured to compare the risk score to a threshold to determine whether the risk score of the user is greater or less than the threshold. If the risk score is greater than the threshold, the risk may be too great. The risk score may be a probability of the user having the infectious disease. The score can be based on historical activities of the user, whether the user has come into contact with infected individuals, whether the user has been tested for the infectious disease, whether the user has been present in high infection areas, etc.

Figure 10:
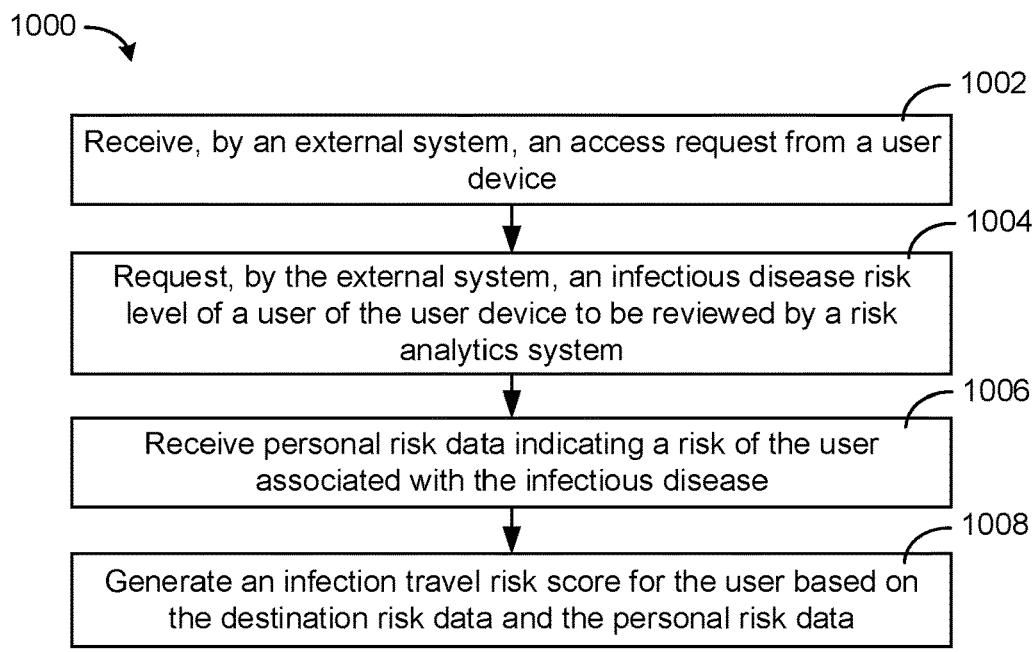
FIG. 10 is a flow diagram of a process of performing risk scoring by the risk analytics system of FIG. 1 for the external system of FIG. 9, according to an exemplary embodiment.

Referring now to FIG. 10, a process 1000 of performing risk scoring by the risk analytics system of FIG. 1 for the external system of FIG. 9 is shown, according to an exemplary embodiment. The process 1000 can be performed by the components of FIG. 9, e.g., the user device 904, the external system 906, and/or the risk analytics system 110. However, the process 1000 can be performed by any computer system or device described herein.

In step 1002, the external system 906 receives an access request from a user device 904. The access request can be triggered by a user requesting some sort of access, e.g., entry into a country, entry into a building, approval to work on-premises, inclusion in a physical meeting, etc. In step 1004, the external system 906 requests an infectious disease risk level of the user of the user device 904 to be reviewed by the risk analytics system 110. The request can further indicate the review or approval criteria that should be applied by the risk analytics system 110.

In step 1006, the risk analytics system 110 can receive personal risk data indicating a risk of the user associated with the infectious disease from the private information database 902. In step 1008, the risk analytics system 110 can generate a risk score based on the personal risk data received in the step 1006. The risk analytics system 110 can determine what level of risk the user poses based on where the user has recently been located (e.g., in high infection geographic areas or low infection geographic areas), has come into contact with an infected individual, etc. The risk analytic system 110 can provide a score and/or a result of a comparison of the score to a threshold to the external system 906. In some embodiments, the risk scoring can include generating an infection travel risk score by the travel application 124.

Figure 11:
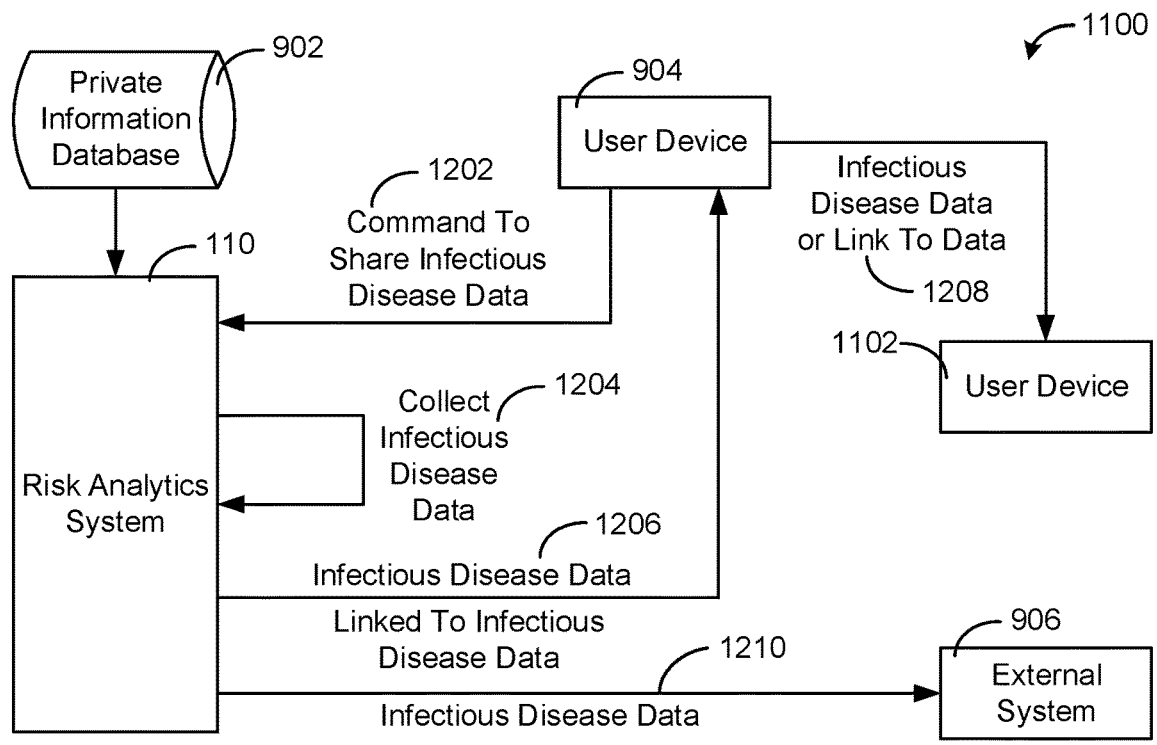
FIG. 11 is a block diagram of the risk analytics system of FIG. 1 sharing infectious disease data with another user device or the external system of FIG. 9 based on a command received from a user device, according to an exemplary embodiment.

Referring now to FIG. 11, a system 1100 of the risk analytics system 110 sharing infectious disease data with another user device 1102 or the external system 906 based on a command received from the user device 1102 is shown, according to an exemplary embodiment. The data sharing of FIG. 11 illustrates a user device sharing infectious disease data to another user device or another external system. However, the data sharing can be performed between two employees (e.g., peer to peer), an employer and a partner system, a user and an airline, a user and a hospitality entity, etc.

In some embodiments, the system 110 can facilitate a sharing feature for the user device 904 via a message (e.g., a text message, an email, etc.). The user deice 904 shares a risk score or disease data with other users, e.g., the user device 1102. Furthermore, the risk analytics system 110 can facilitate data sharing with outside systems, e.g., the external system 906. For example, if the user associated with the user device 904 is visiting a campus, the user may share their infectious disease risk data with the external system of the campus.

As another example, a healthcare facility could receive infectious disease data from the risk analytics system 110 to help identify what is wrong with a patient. For example, if a user has been present in a particular country where an infectious disease is present, the infectious disease data received from the risk analytics system 110 could be used by a doctor or nurse to identify what is wrong with the patient. In some embodiments, the system 1100 facilitates bi-directional data sharing between a testing lab, a hospital, and/or a user.

In some embodiments, the infectious disease data shared by the risk analytics system 110 is a credential of a user of the user device 904. The credential can be a credential that gives an anonymized risk score for the user of the user device 904 that the user can share with other systems or devices. In some embodiments, the risk analytics system 110 issues an enhanced credential that includes a description of personal data of the user. In some embodiments, the external system 906 first receives a normal credential to determine whether the user meets a threshold. After the system determines that the user meets the threshold, the risk analytics system 110 can expose more information of the user to the system in the form of the enhanced credential. The normal and enhanced credentials can be opted into or opted out of by a user of the user device 904.

In some embodiments, the risk analytics system 110 may issue an antibody credential for a user. If the user has previously caught an infectious disease but has built up the antibodies to be immune to the infectious disease, the risk analytics system 110 may issue an antibody credential to the user that can be shared with other systems. The antibody credential can be generated in response to receiving antibody data from a medical testing system that may process an antibody test result of a user.

The risk analytics system 110 can be configured to collect infectious disease data from the private information database 902. The infectious disease data can be associated with a user of the user device 904, e.g., indicate a travel history of the user, indicate a risk level of the user, indicate what other individuals the user has come into contact with, include the health data streams, the risk data streams, etc. The risk analytics system 110 can share the infectious disease data with the user device 904 in response to receiving a request. In some embodiments, the risk analytics system 110 generates a link to the infectious disease data and provides the user device 904 with the link so that the user device 904 can share the link with other devices, e.g., the user device 1102.

In some embodiments, the risk analytics system 110 performs scoring based on the infectious disease data to generate a risk level or risk credential for the user of the user device 904. The risk scoring can be the same or similar to the risk scoring described with reference to FIGS. 9-10.

Figure 12:
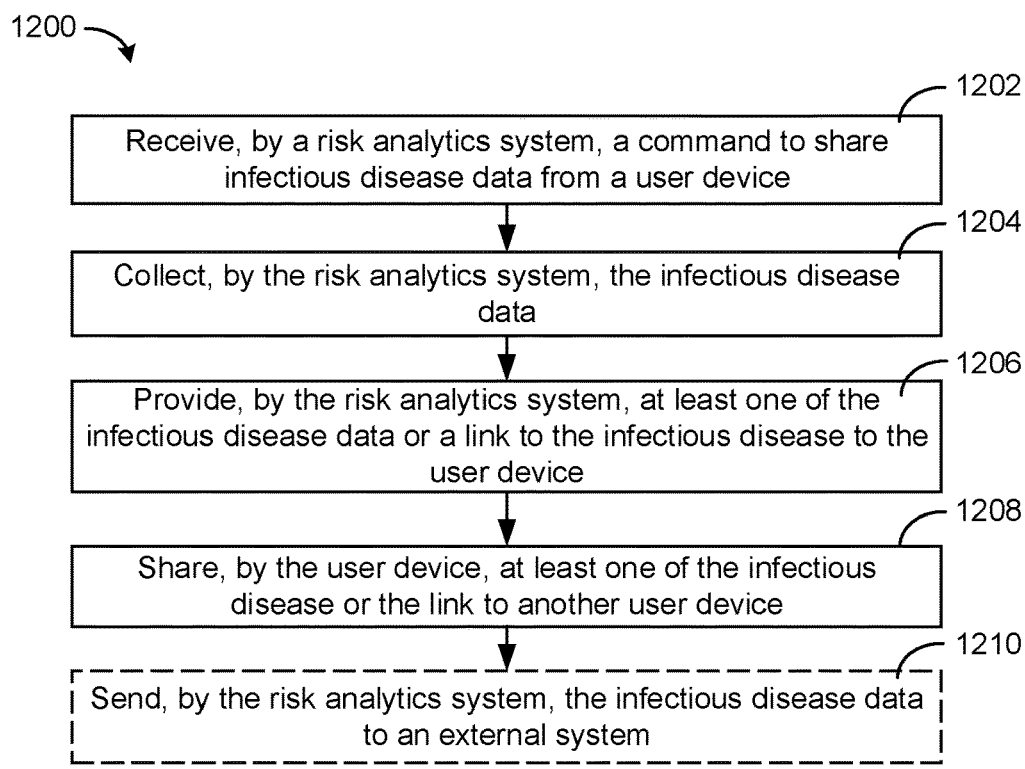
FIG. 12 is a flow diagram of a process of sharing infectious disease data with another user device or the external system of FIG. 9 based on a command received from the user device of FIG. 11, according to an exemplary embodiment.

Referring now to FIG. 12, a flow diagram of a process 1200 of sharing infectious disease data with another user device or the external system 906 based on a command received from the user device 904 is shown, according to an exemplary embodiment. The process 1200 can be performed by the components of FIG. 11, e.g., the user device 904, the external system 906, the user device 1102, and/or the risk analytics system 110. However, the process 1200 can be performed by any computer system or device described herein.

In step 1202, the risk analytics system 110 receives a command to share infectious disease data from the user device 904. The command can indicate that a user of the user device 904 has given approval to share private data of the user with other users and/or systems. In some embodiments, the command indicates particular users and/or systems that the user would like to share the infectious disease data with.

In response to the approval received in the step 1202, the risk analytics system 110 can collect infectious disease data in step 1204. In some embodiments, the risk analytics system 110 collects risk data of the user, e.g., travel data, what hotels the user has stayed at, whether the user has tested positive or negative for an infectious disease, etc. The risk data can further indicate scores, e.g., a risk score calculated by the risk analytics system 110 indicating how likely the user is to infect others with an infectious disease. In some embodiments, collecting the infectious disease data includes collecting an infection travel risk score determined by the travel application 124 from the private information database 902.

In step 1206, the risk analytics system 110 can provide at least one of the infectious disease data or a link to the infectious disease to the user device 904. The infectious disease data can be the data collected and/or determined in the step 1204 by the risk analytics system 110. In some embodiments, the risk analytics system 110 generates a webpage or another data storage element that stores the infectious disease data. The risk analytics system 110 can provide a link to the webpage or other data storage element to the user device 904. In some embodiments, any user and/or particular user accounts can access the link. In step 1208, the user of the user device 904 can share the infectious disease data and/or a link to the infectious disease data with the user device 1102 and/or the external system 906. In some embodiments, in step 1210, the risk analytics system 110 sends the infectious disease data directly to the external system 906 and/or the user device 1102.

Figure 13:
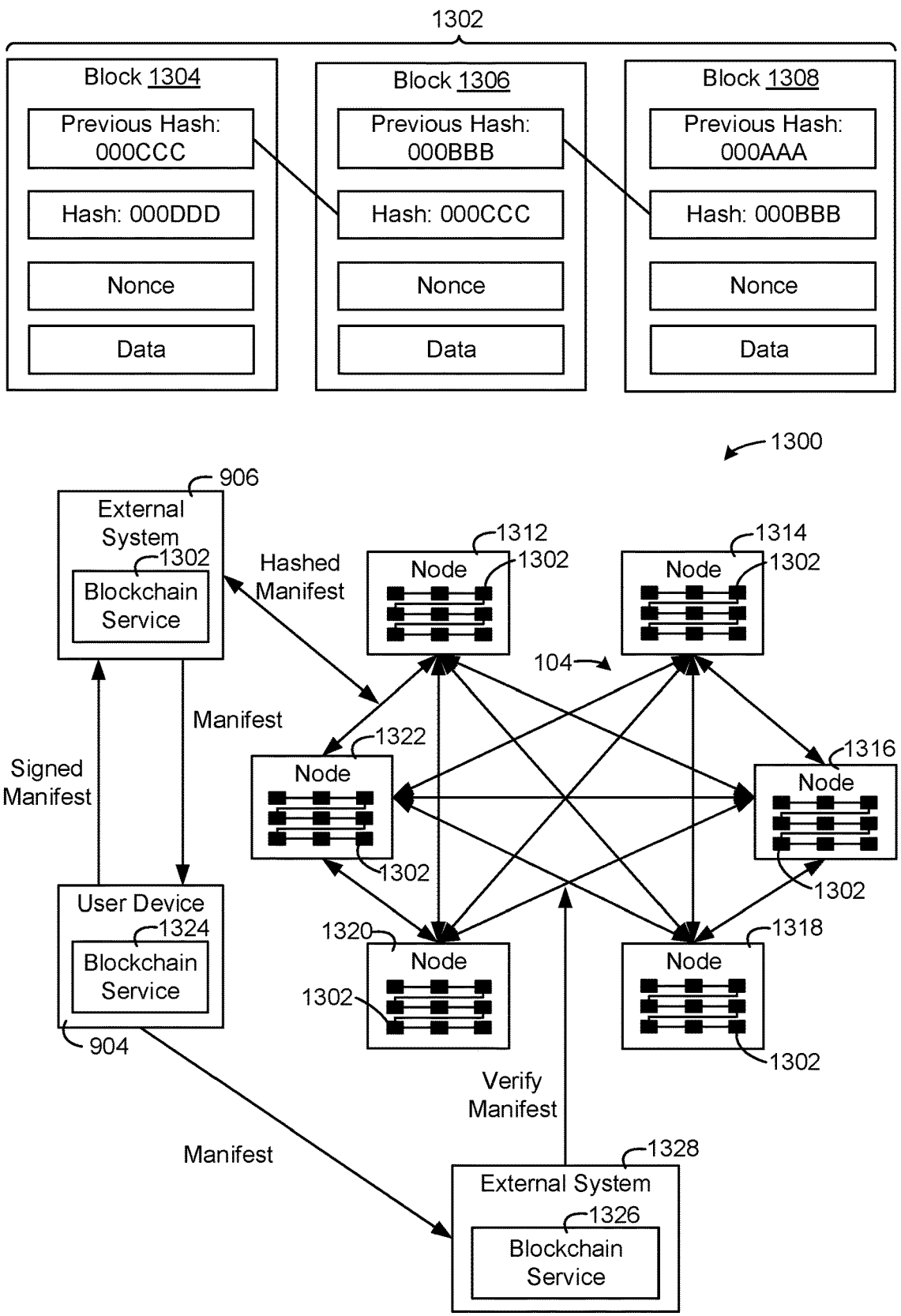
FIG. 13 is a block diagram of a manifest indicating user activity of the user of the user device of FIG. 11 being added to a blockchain database, according to an exemplary embodiment.

Referring now to FIG. 13, a system 1300 configured to add a manifest indicating user activity of the user of the user device to a blockchain 1302 is shown, according to an exemplary embodiment. The system 1300 includes a number of nodes 1312-1322 communicating via the network 104. The nodes 1312-1322 can be various computer systems, devices, servers, etc. In some embodiments, the nodes 1312-1322 are the services and systems described in FIG. 1 and elsewhere herein.

The nodes 1312-1322 are shown to include the blockchain 1302. The blockchain 1302 can be a chain of data blocks where each data block is linked to a previous block, thus, forming a chain. The chain may be a chain of sequentially ordered blocks. In some embodiments, the blockchain 1302 is a private blockchain that is accessible to only particular systems with proper access credentials. In some embodiments, the blockchain 1302 is a public blockchain that is accessible by any system.

The blockchain database 1302 can include any number of blocks and new blocks can be added to the blockchain database 1302 by the nodes 1312-1322 and/or by any other system in communication with the nodes 1312-1322. Three blocks of the blockchain database 1302 are shown in FIG. 13, block 1304, block 1306, and block 1308. Each block is shown to include a nonce, data, a hash, and a hash of the previous block in the chain. The blockchain 1302 is illustrated right to left, that is, the rightmost block is the oldest block shown in FIG. 13 while the leftmost block is the newest block shown in FIG. 13. The data of each block can be private infectious disease data of a user, travel data of the user, health data of the user, data of the health data streams, data of the risk data streams, etc.

The blocks 1304-1308 are shown to include a nonce value. The nonce value can be a value that when hashed with the data of the block and the previous hash, in addition to other information, results in a hash that meets a difficulty requirement. In FIG. 13, the hashes are shown as hexadecimal numbers. In FIG. 13, the difficulty requirement is that the first three values of each hash are zero but any difficulty requirement for the hashes can be utilized in the system 1300. Any of the nodes 1312-1322 can attempt to generate a block with a hash value that meets the difficulty requirement. In some embodiments, some and/or all of nodes 1312-1322 operate to generate a hash value for a new block to be added to the blockchain 1302. If one of the nodes 1312-1322 generates a hash that meets the difficulty requirement, that node can add the block to the blockchain 1302 and notify the other nodes of the solved block so that the other nodes can also add the solved block to the blockchain 1302 that each of the other nodes stores.

The blockchain 1302 can be configured to store user scores, infectious disease data, and/or private data of a user. The blockchain 1302 can be utilized to validate risk scores and/or infectious disease data of a user. In some embodiments, the blockchain 1302 is a distributed ledger for a network of systems, e.g., for restaurants, retail businesses, commercial businesses, car rental services, taxi services, rideshare services, etc. for communicating infectious disease data in a trusted network of systems. In some embodiments, the blockchain 1302 can be used to distribute a history of user events or activities, risk flags, infectious disease risk scores for users, and/or a token or data that provides that a user have been avoiding risky places and risky activity. In some embodiments, businesses and/or other entities may provide a user with different levels of access to locations and/or geographic areas based on a score of a user.

The blockchain 1302 can help make private data anonymous but widely accessible and available to other systems if a user wishes for the data to be shared. The blockchain 1302 can be used to prove that private data of a user stored in the blockchain 1302 is not being tampered with. The blockchain 1302 can be a private blockchain, a public blockchain, and/or a combination of a private and a public blockchain. A public blockchain can be an open source blockchain while a private blockchain may have one or multiple defined entities controlling the public blockchain.

In some embodiments, the system 1300 can be configured to capture and store events in the blockchain 1302. The events can be stored as the data within the blocks of the blockchain, e.g., each block can store one or a set of events. In response to an event occurring, the system 1300 can add a new block including data for the event.

In some embodiments, the external system 906, via a blockchain service 1302 run by the external system 906, generates a manifest for an event. The manifest may be a data file describing an activity that a user associated with the user device 904 has performed and/or engaged in. For example, the manifest may describe a stay at a hotel, a visit to a restaurant, a ride in a car of a rideshare service, a flight taken by the user, a bus ridden by the user, etc. The manifest may include a description of the activity, an identification of the user performing the activity (e.g., an anonymous user identifier tied back to the user), a date of the activity, a beginning time of the activity, an ending time of the activity, and/or any other data.

The manifest can be generated by the external system 906 for the user of the user device 904 and provided by the external system 906 to the user device 904. The external system 906 can be a system for a hotel and can generate the manifest for an overnight stay of the user of the user device 904. In some embodiments, the external system 906 can be a system of a restaurant and can generate the manifest for a dining visit of the user of the user device 904. The user device 904 can sign the manifest with a private key of the user device 904. The private key may be linked to a public identifier, a public key, associated with the user device 904. The user device 904 can return the signed manifest to the external system 906.

In some embodiments, a blockchain service 1324 of the user device 904 signs the manifest received from the external system 906 and returns the manifest to the external system 906. Furthermore, the blockchain service 1324 can maintain a log of manifests for all events of the user. When the user of the user device 904 needs to verify a past event, e.g., a particular manifest, with another system, the external system 1328, the blockchain service 1324 can provide the manifest (or a portion of the manifest log or the entire manifest log) to the external system 1328 for verification. The verification performed by the external system 1328 can be performed by the blockchain service 1326.

In response to receiving a signed manifest from the user device 904, the external system 906 can sign the manifest received from the user device 904. In some embodiments, the external system 906 can sign the manifest before providing the manifest to the user device 904 for signature by the user device 904. The signature by the external system 906 can verify that the external system 906 is the source of the manifest. The external system 906 can sign the manifest with a private key. Furthermore, the external system 906 can hash the signed manifest. The external system 906 can be configured to perform any type of hashing algorithm, e.g., MD5, SHA-2, CRC32, etc. The external system 906 can be configured to add the hashed manifest to the blockchain 1302.

In some embodiments, the user device 904 can validate a manifest with another external system. For example, the user of the user device 904 may stay in a hotel associated with the external system 906. The user may then wish to eat a restaurant associated with the external system 1328. However, the external system 1328 may first verify what hotel the user associated with the user device 904 has stayed in before the user associated with the user device 904 is allowed to eat at the restaurant. The user device 904 can provide the manifest to the external system 1328.

The external system 1328 can verify the manifest received from the user device 904 with the blockchain 1302. The external system 1328 can hash the manifest received from the user device 904 to determine that the hashed manifest received from the user device 904 matches the hashed manifest stored in the blockchain 1302. Furthermore, the external system 1328 can verify the signature of the manifest stored in the blockchain 1302 and/or the manifest received from the user device 904 with a public key of the user device 904. The external system 1328 can verify a signature of the external system 906 of the manifest stored in the blockchain 1302 and/or the manifest received from the user device 904 with a public key of the external system 906.

The external system 1328, via the signed and hashed manifest of the blockchain 1302, can verify that the manifest of the blockchain 1302 identifies the user of the user device 904. The signature of the manifest provided by the user device 904 included within the blockchain 1302 can verify that the user associated with the user device 904. The signature does not expose the identity of the user of the user device 904 but can be used by the external system 1328 to identify the user and verify that an event claimed to be associated with the user is actually associated with the user.

In some embodiments, the private log of manifests stored by the user device 904 can be used to validate activities with employers (e.g., to determine whether the user provides a risk of spreading an infectious disease and whether the user should return to work), health agencies (e.g., to determine whether the user provides a risk of spreading an infectious disease and/or whether the user should be allowed to enter a country or geographic district), and/or any other entity or system. Furthermore, because the information stored within the blockchain 1302 does not expose private information of the user of the user device 904 but only includes signed and hashed data, the user of the user device 904 can choose what systems and/or entities that the user provides their manifest log to. In this regard, the history of events associated with the user of the user device 904 are kept private but can be verified through the blockchain 1302 in response to the user providing their manifest log for verification.

In some embodiments, the manifest based blockchain event tracking of the system 1300 can be utilized to track a group of users. For example, a company may employ the system of 1300 to track employees, a state may use the system 1300 to track the activities of its citizens, a hospital may use the system 1300 to track the activities of its patients, etc. The events can indicate the locations of a user, the restaurant visits of a user, the transit use of the user, etc. Based on the events stored within the blockchain 1302, the risk analytics system 110 (e.g., the travel application 124 performing the process 800 described with reference to FIG. 8) can generate an infectious disease risk score indicating how likely a user is to spread an infectious disease. The blockchain 1302 can store travel locations of a user at multiple places throughout a day, week, month, and/or year. The travel application 124 can generate the risk score based on the risk levels associated with various geographic locations, retail stores visited by the user, hotels stayed in, restaurants that the user has eaten in, etc.

Figure 14:
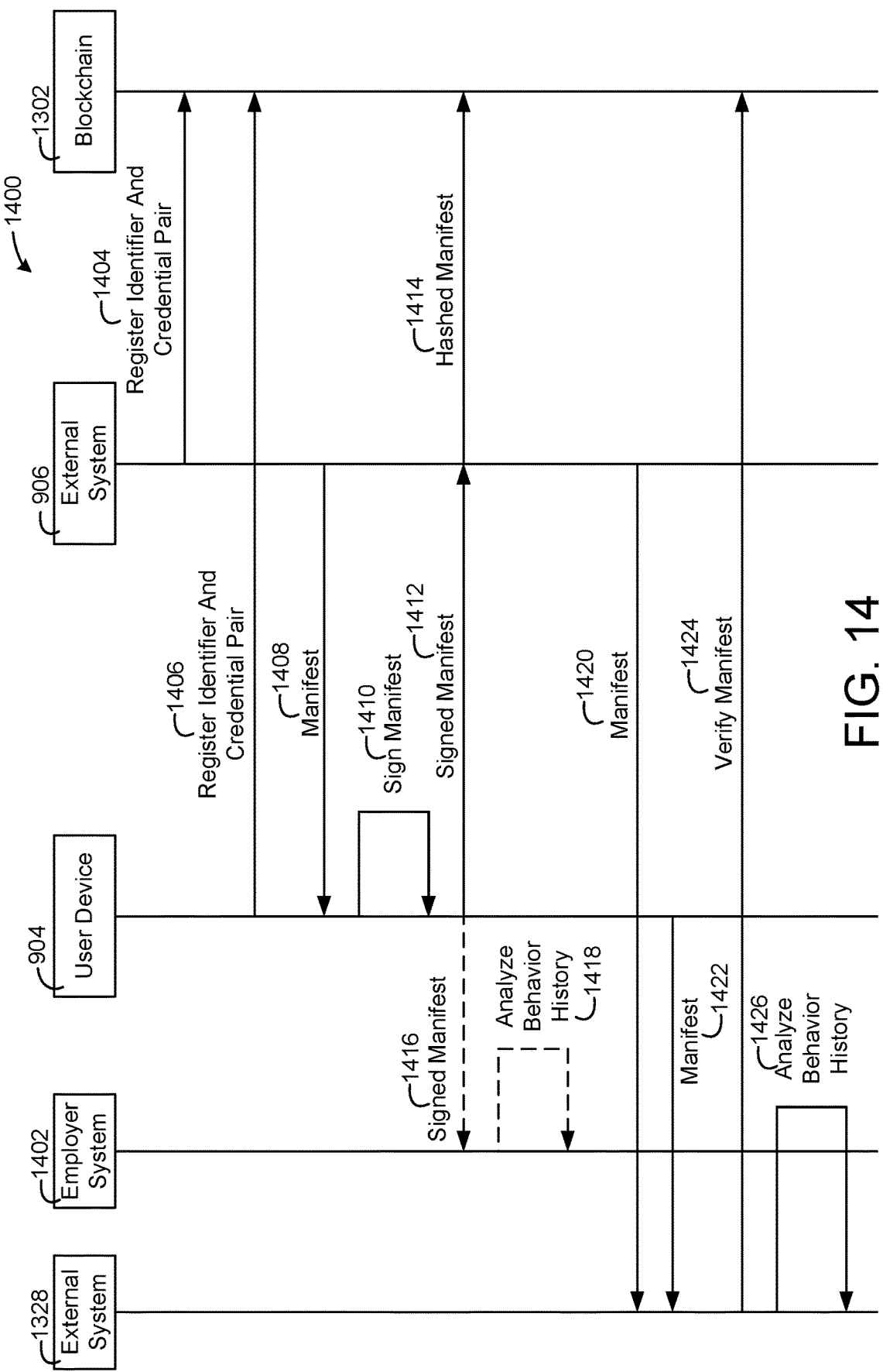
FIG. 14 is a flow diagram of a process where the manifest of FIG. 13 is added to the blockchain database of FIG. 13 and used to verify user activity of the user of the user device of FIG. 11, according to an exemplary embodiment.

Referring now to FIG. 14, a process 1400 where a manifest is added to the blockchain 1302 and used to verify user activity of the user of the user device 904 is shown, according to an exemplary embodiment. The systems, devices, and databases shown performing the process 1400 can be the systems, devices, and databases described with reference to FIG. 13. Furthermore, FIG. 14 includes an employer system 1402 which may be a system associated with an employer of the user of the user device 904. The external system 1328, the employer system 1402, the user device 904, the external system 906, and/or the blockchain 1302 can perform some and/or all of the steps of the process 1400.

The process 1400 can utilize the blockchain 1302 to document the traveler behavior of individuals. Due to the private nature of travel, some individuals may not want to be tracked publically but would rather prefer to be tracked indirectly and/or privately. If a user opts in for indirect tracking, the travel behavior of the user can be identified with information stored in the blockchain 1302 in combination with information carried in the user device 904 to provide a verifiable track and trace of the individual. The blockchain 1302 can provide a signed artifact, e.g., the manifest, the can be used to verify the activity of the user of the user device 904.

In step 1404, the external system 906 can register an identifier and credential pair with the blockchain 1302 and/or a service that manages the blockchain 1302. The identifier may be a number, text, and/or an alphanumeric value that uniquely identifies the external system 906. Furthermore, the external system 906 can further register a credential pair including a public key and a private key with the blockchain 1302. In some embodiments, the identifier of the external system 906 is the public key. The public key and the private key can be used to sign data and/or documents and verify the signature of the external system 906, e.g., the external system 906 can sign the data with the private key while another entity (e.g., the external system 1328) can verify the signature of the data with the public key.

In step 1406, the user device 904 can register an identifier and a credential pair with the blockchain 1302 and/or a service that manages the blockchain 1302. The identifier may be a number, text, and/or an alphanumeric value that uniquely identifies the user device 904. Furthermore, the user device 904 can further register a credential pair including a public key and a private key with the blockchain 1302. In some embodiments, the identifier of user device 904 is the public key. The public key and the private key can be used to sign data and/or documents and verify the signature of the user device 904, e.g., the user device 904 can sign the data with the private key while another entity (e.g., the external system 1328) can verify the signature of the data with the public key.

In step 1408, the external system generates a manifest and provides the manifest to the user device 904. The user of the user device 904 may perform an event, e.g., a travel activity associated with travel of the user. For example, the user of the user device 904 may stay at a hotel associated with the external system 906. The manifest may be a receipt of the stay of the user of the user device 904. The receipt, the manifest, can include metadata describing the stay of the user, e.g., the name of the hotel, the room number of the room that the user stayed in, the check-in date, the check-out date, etc. In some embodiments, the manifest is signed by the external system 906 with a private key of the external system 906 before the manifest is provided to the user device 904.

In step 1410, the user device 904 signs the manifest with the private key of the user device 904. In some embodiments, the user reviews the manifest via a display screen of the user device 904 to verify that the information of the manifest is accurate and provides the user device 904 with an authorization to sign the manifest via an input device of the user device 904. In step 1412, the user device 904 provides the signed manifest to the external system 906.

In step 1414, the external system 906 hashes the manifest (e.g., with or without the signatures of the external system 906 and the user device 904) and stores the hashed manifest in the blockchain 1302. The manifest can be stored with a date and time. The data and time may be provided by a trusted time keeping system.

Steps 1416 and 1418 are optional and are shown in dashed lines. In step 1416, the signed manifest can be provided to the employer system 1402. If the user is opted into a private verification/tracking system, e.g., with the employer system 1402, the manifest could be uploaded to the employer system 1402 for record keeping and storage. The employer can verify the authenticity of the manifest if desired by looking for the date and/or time, an optional transaction identifier, and/or any other metadata, and verify, via the blockchain 1302, that the hash was in fact stored in the blockchain 1302 for that manifest In step 1418, the employer system 1402 can analyze a behavior history of the user. The employer system 1402 can utilize the uploaded manifest to determine if the user has traveled to a hotspot during a respective time period (e.g., during the last two weeks if the incubation period for the virus is two weeks). The employer system 1402 can also use the manifest to auto-populate the expenses reporting system for the user. In some embodiments, the external system 906 can provide the manifest directly to the employer system 1402. For example, the external system 906 and an employer may have a contract relationship and the external system 906 could upload the manifest to employer systems automatically and not require the user to do so.

In steps 1404-1414, no user identifiable information is shared about the user of the user device 904 in the blockchain 1302. While the identifier of the user device 904 and/or the identifier of the external system 906 may be stored in the manifest, the exact name of the user of the user deice 904 and/or the name of the external system 906 may not be stored in the manifest. The only information that is stored in the blockchain 1302 is the record that the external system 906 added to the blockchain, the hash of the manifest and the date and time the manifest was signed, and other relevant and non-identifying metadata.

If the external system 1328 (e.g., a trusted third party such as a company) wanted to verify the location of an individual for a period of time, the external system 1328 could send a request for a manifest record of a particular time and/or manifest records of a particular time period. The user of the user device 904 could respond to the request by the external system 1328 and send the external system 1328 the manifest (or manifest records for a requested time period) via the user device 904 (or the external system 906 could send the external system 1328 the manifest) (steps 1420 and/or 1422). The user device 904 could identify one or multiple manifests that are associated with a time within the time period specified by the external system 1328 and respond to the external system 1328 with the identified manifest or manifests.

In step 1424, the external system 1328 can verify the manifest received from the user device 904. The external system 1328 can use public keys of the user device 904 and/or the external system 906 to verify the authenticity of the manifest stored in the blockchain 1302 and/or the manifest received from the user device 904. For example, the external system 1328 can verify signatures of the user device 904 and/or the external system 906 with public keys of the user device 904 and/or the external system 906 respectively.

Furthermore, the external system 1328 can compare the received manifest to the manifest of the blockchain 1302 to verify that the received manifest matches the copy of the manifest stored in the blockchain 1302. In some embodiments, because the copy of the manifest stored in the blockchain 1302 is hashed, the external system 1328 may first hash the manifest received from the user 904 and compare the received hashed manifest to the hashed manifest stored in the blockchain 1302 to verify that the two hashed manifests match. The hashing algorithms used by the external system 1328 and/or the external system 906 may be the same.

In step 1426, the external system 1328 can analyze the behavior of the user indicated by the manifest. The blockchain 1302 and manifest records could also be used to provide an attestation that the user has not been exposed to a hotspot area without divulging their travel data. For example, a hotel may require attestation that a user has not been in a hotspot area before the user is permitted to stay at a hotel. A third party attestation service could be used that would allow the user to upload their manifests during the requested time period (data only uploaded to the third party service not the company wanting the verification). The third party attestation service would verify the authenticity of the manifests and based on the location and/or date the traveler was at each location. This information could be compared against a database that contains information on the risk of geographic areas at the time periods when the user visited those areas (e.g., number of infected individuals that were at those locations, etc.) and a score could then be generated and securely sent to a requestor. This would allow the requestor to understand the risk profile of the traveler but in a way in which they have no information or details about where that individual has traveled but instead of an attestation from a third party service Configuration of Exemplary Embodiments The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

In various implementations, the steps and operations described herein may be performed on one processor or in a combination of two or more processors. For example, in some implementations, the various operations could be performed in a central server or set of central servers configured to receive data from one or more devices (e.g., edge computing devices/controllers) and perform the operations. In some implementations, the operations may be performed by one or more local controllers or computing devices (e.g., edge devices), such as controllers dedicated to and/or located within a particular building or portion of a building. In some implementations, the operations may be performed by a combination of one or more central or offsite computing devices/servers and one or more local controllers/computing devices. All such implementations are contemplated within the scope of the present disclosure. Further, unless otherwise indicated, when the present disclosure refers to one or more computer-readable storage media and/or one or more controllers, such computer-readable storage media and/or one or more controllers may be implemented as one or more central servers, one or more local controllers or computing devices (e.g., edge devices), any combination thereof, or any other combination of storage media and/or controllers regardless of the location of such devices.

What is claimed:

1. A system comprising one or more memory devices having instructions stored thereon, that, when executed by one or more processors, cause the one or more processors to:
   receive travel data associated with a travel plan of a user indicating one or more travel destinations;
   receive destination risk data indicating a destination risk of the one or more travel destinations associated with transmission of an infectious disease;
   receive personal risk data indicating a risk of the user associated with the infectious disease;
   receive a manifest from a user device of the user representing historical travel activity performed by the user with a travel service;
   receive a second manifest from aa blockchain, wherein the second manifest is a copy of the manifest, wherein the second manifest is stored in the blockchain by an external system to create a record of the historical travel activity performed by the user;
   validate the manifest received from the user device with the second manifest of the blockchain; and
   generate an infection travel risk score for the user based on the destination risk data, the historical travel activity represented by the manifest, and the personal risk data.

2. The system of claim 1, wherein the instructions cause the one or more processors to generate one or more suggestions to the travel plan based on the infection travel risk score increasing to a value greater than a particular amount caused by at least one of a first change to the destination risk data or a second change to the personal risk data.

3. The system of claim 1, wherein the instructions cause the one or more processors to:
   generate a plurality of travel routes from an originating location to the one or more travel destinations;
   generate infection route risk scores for the plurality of travel routes; and
   perform at least one of:
      generating a suggestion for the user to travel on one of the plurality of travel routes associated with a lowest infection route risk score;
      generating a user interface including an indication of the plurality of travel routes and the infection route risk scores; or
      generating a list including the plurality of travel routes ranked according to the infection route risk scores associated with the plurality of travel routes.

4. The system of claim 1, wherein the personal risk data indicates whether the user has previously contracted and recovered from the infectious disease.

5. The system of claim 1, wherein the instructions cause the one or more processors to:
   receive a request for the infection travel risk score from the external system, wherein the external system sends the request to the one or more processors in response to the user device of the user requesting access from the external system to a service or location; and
   communicate the infection travel risk score to the external system in response to receiving the request from the external system.

6. The system of claim 1, wherein the instructions cause the one or more processors to:
   receive a request to share the infection travel risk score from the user device of the user with a second user device or the external system; and
   responsive to receiving the request, perform at least one of:
      sending the infection travel risk score to the user device, the second user device, or a second external system; or
      generating a shareable link to a data source storing the infection travel risk score and send the shareable link to the user device.

7. The system of claim 1, wherein the second manifest includes a first signature of the user device and a second signature of the external system;
   wherein the instructions cause the one or more processors to:
      determine that the first signature is authentic with a first public key of the user device; and
      determine that the second signature is authentic with a second public key of the external system.

8. The system of claim 1, wherein the second manifest is hashed by the external system;
   wherein the instructions cause the one or more processors to validate the manifest received from the user device by determining that the manifest matches the second manifest by hashing the manifest received from the user device and comparing a hash of the manifest received from the user device to the second manifest hashed by the external system.

9. The system of claim 1, wherein the instructions cause the one or more processors to:
   generate a travel itinerary for the user based on the travel data and risk data associated with the travel plan and provide the travel itinerary to the user via a user interface of the user device;
   generate one or more suggested updates to the travel itinerary based on changes in the risk data to dynamically account for changes in the risk data as the user is traveling; and
   provide the one or more suggested updates to the user via the user interface of the user device.

10. The system of claim 9, wherein the instructions cause the one or more processors to generate the travel itinerary based on a plurality of disparate factors including travel modes, travel destinations, and stops along a travel route.

11. The system of claim 9, wherein the risk data indicates disease infection risk indicating a likelihood of the user contracting the infectious disease.

12. The system of claim 9, wherein the risk data is received by the one or more processors as risk events from at least one of an event notification system, a contact tracing system, or a health authority system.

13. The system of claim 9, wherein the risk data is contact tracing data, wherein the contact tracing data indicates at least one of one or more past locations or one or more future locations of a person infected by the infectious disease;
   wherein the instructions cause the one or more processors to perform at least one of generating the travel itinerary to include one or more transportation selections that avoid at least one of the one or more past locations or the one or more future locations of the person infected by the infectious disease or updating a value of the infection travel risk score based on the contact tracing data.

14. The system of claim 9, wherein the instructions cause the one or more processors to:
   determine risk values associated with a plurality of dining options;
   select one or more dining options from the plurality of dining options based on the risk values associated with the plurality of dining options; and
   cause the travel itinerary to include the one or more dining options.

15. The system of claim 9, wherein the instructions cause the one or more processors to:
   determine risk values associated with a plurality of overnight stay accommodation options;
   select one or more overnight stay accommodations from the plurality of overnight stay accommodation options based on the risk values associated with the plurality of overnight stay accommodation options; and
   cause the travel itinerary to include the one or more overnight stay accommodations.

16. The system of claim 9, wherein the risk data indicates a threat level associated with a plurality of geographic areas;
   wherein the instructions cause the one or more processors to generate the travel itinerary by determining one or more travel routes through one or more low risk geographic areas associated with threat levels less than one or more other high risk geographic areas;
   wherein the threat levels associated with the plurality of geographic areas indicate a disease infection level of people within the plurality of geographic areas.

17. The system of claim 9, wherein the travel itinerary comprises one or more transportation selections;
   wherein the instructions cause the one or more processors to select the one or more transportation selections from a plurality of transportation options based on transportation risk data associated with the plurality of transportation options.

18. The system of claim 17, wherein the one or more transportation selections include one or more car rental selections;
   wherein the instructions cause the one or more processors to select the one or more car rental selections from a plurality of car rental options based on a health safety ratings of the plurality of car rental options.

19. The system of claim 17, wherein the one or more transportation selections include one or more flight transportation selections;
   wherein the transportation risk data associated with the plurality of transportation options includes one or more of a length of a flight layover, a distance between two flight gates of a connecting flight, a likelihood of the user needing to eat during the traveling of the user, or an indication of infected individuals booked for a particular flight.

20. A method comprising:
   receiving, by a processing circuit, travel data associated with a travel plan of a user indicating one or more travel destinations;

receiving, by the processing circuit, destination risk data indicating a destination risk of the one or more travel destinations associated with transmission of an infectious disease;

receiving, by the processing circuit, personal risk data indicating a risk of the user associated with the infectious disease;

receiving, by the processing circuit, a manifest from a user device of the user representing historical travel activity performed by the user with a travel service;

receiving, by the processing circuit, a second manifest from a blockchain, wherein the second manifest is a copy of the manifest, wherein the second manifest is stored in the blockchain by an external system to create a record of the historical travel activity performed by the user;

validating, by the processing circuit, the manifest received from the user device with the second manifest of the blockchain; and generating, by the processing circuit, an infection travel risk score for the user based on the destination risk data, the historical travel activity represented by the manifest, and the personal risk data.

21. The method of claim 20, further comprising generating, by the processing circuit, one or more suggestions to the travel plan based on the infection travel risk score increasing to a value greater than a particular amount caused by at least one of a first change to the destination risk data or a second change to the personal risk data.

22. The method of claim 20, further comprising:
generating, by the processing circuit, a plurality of travel routes from an originating location to the one or more travel destinations;
generating, by the processing circuit, infection route risk scores for the plurality of travel routes; and
performing, by the processing circuit, at least one of:
generating a suggestion for the user to travel on one of the plurality of travel routes associated with a lowest infection route risk score;
generating a user interface including an indication of the plurality of travel routes and the infection route risk scores; or
generating a list including the plurality of travel routes ranked according to the infection route risk scores associated with the plurality of travel routes.

23. The method of claim 20, further comprising:
generating, by the processing circuit, a travel itinerary for the user based on the travel data and risk data associated with the travel plan and provide the travel itinerary to the user via a user interface of the user device;
generating, by the processing circuit, one or more suggested updates to the travel itinerary based on changes in the risk data to dynamically account for changes in the risk data as the user is traveling; and
providing, by the processing circuit, the one or more suggested updates to the user via the user interface of the user device.

24. The method of claim 23, wherein the risk data indicates disease infection risk indicating a likelihood of the user contracting the infectious disease.

25. The method of claim 23, wherein the risk data is received by the processing circuit as risk events from at least one of an event notification system, a contact tracing system, or a health authority system.

26. A system comprising:
one or more memory devices having instructions stored thereon; and
one or more processors configured to execute the instructions, wherein the instructions cause the one or more processors to:
receive travel data associated with a travel plan of a user indicating one or more travel destinations;
receive destination risk data indicating a destination risk of the one or more travel destinations associated with transmission of an infectious disease;
receive personal risk data indicating a risk of the user associated with the infectious disease;
receive a manifest from a user device of the user representing historical travel activity performed by the user with a travel service;
receive a second manifest from a blockchain, wherein the second manifest is a copy of the manifest, wherein the second manifest is stored in the blockchain by an external system to create a record of the historical travel activity performed by the user;
validate the manifest received from the user device with the second manifest of the blockchain; and
generate an infection travel risk score for the user based on the destination risk data, the historical travel activity represented by the manifest data, and the personal risk data.

27. The system of claim 26, wherein the instructions cause the one or more processors to generate one or more suggestions to the travel plan based on the infection travel risk score increasing to a value greater than a particular amount caused by at least one of a first change to the destination risk data or a second change to the personal risk data.

28. The system of claim 26, wherein the instructions cause the one or more processors to:
generate a plurality of travel routes from an originating location to the one or more travel destinations;
generate infection route risk scores for the plurality of travel routes; and
perform at least one of:
generating a suggestion for the user to travel on one of the plurality of travel routes associated with a lowest infection route risk score;
generating a user interface including an indication of the plurality of travel routes and the infection route risk scores; or
generating a list including the plurality of travel routes ranked according to the infection route risk scores associated with the plurality of travel routes.

* * * * *